United States Patent [19]

Hepp et al.

[11] Patent Number: 6,114,117
[45] Date of Patent: *Sep. 5, 2000

[54] HOMOGENEOUS DIAGNOSTIC ASSAY METHOD UTILIZING SIMULTANEOUS TARGET AND SIGNAL AMPLIFICATION

[75] Inventors: Jozsef Hepp; Zsolt Lengyel, both of Camarillo; Rajiv Pande, Ventura; Janos Botyanszki; Miklos Sahin-Toth, both of Camarillo, all of Calif.

[73] Assignee: Medical Analysis Systems, Inc., Camarillo, Calif.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/895,495

[22] Filed: Jul. 16, 1997

Related U.S. Application Data

[63] Continuation-in-part of application No. 08/692,825, Jul. 25, 1996, Pat. No. 5,858,665.

[51] Int. Cl.⁷ .............................. C12Q 1/68; C07H 21/02; C07H 21/04; C12N 15/00

[52] U.S. Cl. .......................... 435/6; 536/23.1; 536/24.3; 935/76; 935/77; 935/78

[58] Field of Search ................................ 435/6; 536/23.1, 536/24.3; 935/76, 77, 78

[56] References Cited

U.S. PATENT DOCUMENTS

| | | |
|---|---|---|
| 4,463,090 | 7/1984 | Harris . |
| 4,699,876 | 10/1987 | Libeskind . |
| 5,011,769 | 4/1991 | Duck et al. . |
| 5,118,605 | 6/1992 | Urdea . |
| 5,190,864 | 3/1993 | Giese et al. . |
| 5,283,174 | 2/1994 | Arnold, Jr. et al. .................. 435/6 |
| 5,288,611 | 2/1994 | Kohne . |
| 5,352,775 | 10/1994 | Albertsen et al. . |
| 5,445,942 | 8/1995 | Rabin et al. . |
| 5,462,871 | 10/1995 | Boon-Falleur et al. . |
| 5,470,723 | 11/1995 | Walker et al. . |
| 5,494,796 | 2/1996 | Spears et al. . |
| 5,500,341 | 3/1996 | Spears . |
| 5,508,168 | 4/1996 | Orle et al. . |
| 5,512,444 | 4/1996 | Patard et al. . |
| 5,518,884 | 5/1996 | Spears et al. . |
| 5,527,676 | 6/1996 | Vogestein et al. . |
| 5,529,780 | 6/1996 | Paoletti et al. . |
| 5,532,108 | 7/1996 | Vogelstein . |
| 5,534,438 | 7/1996 | Hayden et al. . |
| 5,536,636 | 7/1996 | Freeman, Jr. et al. . |
| 5,536,638 | 7/1996 | Rossau et al. . |
| 5,565,519 | 10/1996 | Rhee et al. . |
| 5,639,604 | 6/1997 | Arnold, Jr. et al. .................. 435/6 |
| 5,658,737 | 8/1997 | Nelson et al. ........................ 435/6 |
| 5,858,665 | 1/1999 | Hepp et al .......................... 435/6 |

FOREIGN PATENT DOCUMENTS

| | | |
|---|---|---|
| 0123265 | 10/1984 | European Pat. Off. . |
| 0151001 | 8/1985 | European Pat. Off. . |
| 0243797 | 11/1987 | European Pat. Off. . |
| 0330185 | 9/1993 | European Pat. Off. . |
| WO 86/06489 | 11/1986 | WIPO . |
| WO 88/05827 | 8/1988 | WIPO . |
| WO 92 08979 | 5/1992 | WIPO . |
| WO 95/06750 | 3/1995 | WIPO . |
| WO 96/00795 | 1/1996 | WIPO . |

OTHER PUBLICATIONS

Livak et al., PCR Methods and Applications 4 : 357–362 (1995).

Bekkaoui et al., "Cycling probe technology with RNase H attached to an oligonucleotide" *BioTechniques* (1996) 20:240–248.

Betsch, "Nucleic acid amplification–based diagnostics: Barriers to commercialization" *IVD Technology* (Jan. 1995) pp. 22–28.

Compton, "Nucleic acid sequence–based amplification" *Nature* (1991) 350:91–92.

Dirksen et al., "Selective inhibition of RNase H by dextran" *J. Biol. Chem.* (1981) 256:11569–11573.

Gingeras et al., "Hybridization properties of immobilized nucleic acids" *Nucleic Acids Res.* (1987) 15:5373–5390.

Graf, L. et al., "Selective alteration of substrate specificity by replacement of aspartic acid–189 with lysine in the binding pocket of trypsin" *Biochemistry* (1987) 26:2616–2623.

Hermanson, *Bioconjugate Techniques* (1990) Academic Press, New York, Section 3.2 pp. 55–56.

Hermanson, *Bioconjugate Techniques* (1995) Academic Press, New York, pp. 649–651.

Hermanson, *Bioconjugate Techniques* (1996) Academic Press, New York, Section 2.4 pp. 662–664.

Hofstee, "Soluble stoichiometric complexes of DNA with chymotrypsin and trypsin" *Biochim. Biophys. Acta.* (1960) 44:194–195.

(List continued on next page.)

*Primary Examiner*—W. Gary Jones
*Assistant Examiner*—Ethan Whisenant
*Attorney, Agent, or Firm*—Morrison & Foerster, LLP

[57] ABSTRACT

The present invention relates to a method, kit and reagent composition for determining the presence of a target nucleic acid in a sample using a two-stage target cycling reaction. During stage 1 of the reaction, the target nucleic acid hybridizes with a probe nucleic acid to effectuate release of an activator into the assay medium. During stage 2 of the reaction, a target analog-anchor complex is cleaved by the activator, which accomplishes the dual purpose of releasing the target analog into the assay medium, and the initiation of signal generation. The released target analog then restarts the cyclic reaction by binding to a second probe, which effectuates release of a second activator, and so on. This cyclic reaction gives rise to an increase in the amount of signal generated from a single target nucleic acid molecule in the sample, which greatly enhances the level of target detection that can be expected.

34 Claims, 6 Drawing Sheets

OTHER PUBLICATIONS

Houston et al., "The transient inactivation of trypsin by mild acetylation with N–acetylimidazole" *Biochemistry* (1970) 9:156–166.

Kulisek et al., "A chromogenic assay for the detection of plasmin generated by plasminogen activator immobilized on nitrocellulose using a para–nitroanilide synthetic peptide substrate" *Analytical Biochemistry* (1989) 177:78–84.

Lund et al., "Assessment of methods for covalent binding of nucleic acids to magnetic heads, Dynabeads™, and the characteristics on the bound nucleic acids in hybridization reactions" *Nucl. Acids Res.* (1988) 16:10861–10880.

Magee et al., "Specific one–stage method for assay of enterokinase activity by release of radiolabelled activation peptides from $\alpha$–N–[$^3$H]acetyl–trypsinogen and the effect of calcium ions on the enzyme activity" *Biochem J.* (1981) 197:239–244.

Matthews et al., "Analytical strategies for the use of DNA probes" *Analytical Biochemistry* (1988) 169:1–25.

Mifflin et al., "Use and diagnostic application of the polymerase chain reaction (PCR)" Workshop for Forty–Seventh National Meeting, American Association for Clinical Chemistry, Jul. 18, 1995, Anaheim, CA, 30 pages total.

Mir, M. et al., "Chemical modification of buried lysine residues of bovine serum albumin and its influence on protein conformation and bilirubin binding" *Biochim Biophys Acta* (1992) 1119:261–267.

Nelson et al., "Detection of acridinium esters by chemiluminescence" *Nonisotopic DNA Probe Techniques*, (1992) Academic Press, New York, pp. 275–310.

Nilsson et al., "Thin–layer immunoaffinity chromatography with bar code quantitation of C–reactive protein" *Anal. Chem.* (1995) 67:3051–3056.

Owens et al., "Sensitive and rapid diagnosis of potato spindle tuber viroid disease by nucleic acid hybridization" *Science* (1981) 213:670–672.

Product Brochure, "CFLPScan™ Kits: Sensitive detection of mutations in minutes" Boehringer Mannheim Biochemicals (Mar. 1996), 3 pages total.

Product Brochure, "Faster Mutation Analysis" *Ambion, Inc.*, 2130 Woodward Street, #200, Austin, TX 78744–1832, 6 pages total.

Radding, "Helical interactions in homologous pairing and strand exchange driven by RecA protein" *J. Biol. Chem.* (1991) 9:5355–5358.

Robinson et al., "The relation of the $\alpha$–amino group of trypsin to enzyme function and zymogen activation" *Biochemistry* (1973) 12:420–425.

Saiki et al., "Primer–directed enzymatic amplification of DNA with a thermostable DNA polymerase" *Science* (1988) 239:487–491.

Sambrook et al., *Molecular Cloning: A Laboratory Manual, Second Edition* (1989) Cold Spring Harbor Laboratory Press, Chapter 11, pp. 11.1–11.61.

Sambrook et al., *Molecular Cloning: A Laboratory Manual, Second Edition* (1989) Cold Spring Harbor Laboratory Press, Chapter 5, pp. 5.1–5.95.

Southern, "Detection of specific sequences among DNA fragments separated by gel electrophoresis" *J. Mol. Biol.* (1975) 98:503–517.

Stec et al., "Automated solid–phase synthesis, separation, and stereochemistry of phosphorothioate analogues of oligodeoxyribonucleotides" *J. Am. Chem. Soc.* (1984) 106:6077–6079.

Stevens et al., "Real time detection of quantitative PCR using multiple fluorogenic probes" *Clinical Chemistry* (1995) 41:1683. (Abstract 022).

Urdea et al., "Synthesis and characterization of branched DNA (bDNA) for the direct and quantitative detection of CMV, HBV, HCV, and HIV" *Clin. Chem.* (1993) 39:725–726.

Vratsanos et al., "On the mechanism of enzyme action. LXVII. Acetylation of trypsin in organic solvents" *Archives of Biochemistry and Biophysics* (1953) 77:216–226.

Walker, "Inducible DNA repair systems" *Ann. Rev. Biochem.* (1985) 54:425–457.

Wang, "The profile advantage" *Profile Diagnostic Sciences, Inc.*, 510 East 73rd Street, New York, NY 10021, 14 pages total.

West et al., "recA protein promotes homologous–pairing and strand–exchange reactions between duplex DNA molecules" *Proc. Nat. Acad. Sci. USA* (1981) 78:2100–2104.

Wong, *Chemistry of Protein Conjugation and Cross–Linking* (1991) CRC Press, Inc. Boca Raton, Florida. The title page and table of contents are enclosed herewith.

Wu et al., "The ligation amplification reaction (LAR)–amplification of specific DNA sequences using sequential rounds of template–dependent ligation" *Genomics* (1990) 4: 560–569.

Yamashina, "The action of enterokinase on trypsinogen" *Biochim. Biophys. Acta.* (1956) 20:433–434.

Yaron et al., "Intramolecularly quenced fluorogenic susrates for hydrolytic enzymes" *Analytical Biochemistry* (1979) 95:228–235.

Zimmerman et al., "Sensitive assays for trypsin, elastase, and chymotrypsin using new fluorogenic substrates" *Analytical Biochemistry* (1977) 78:47–51.

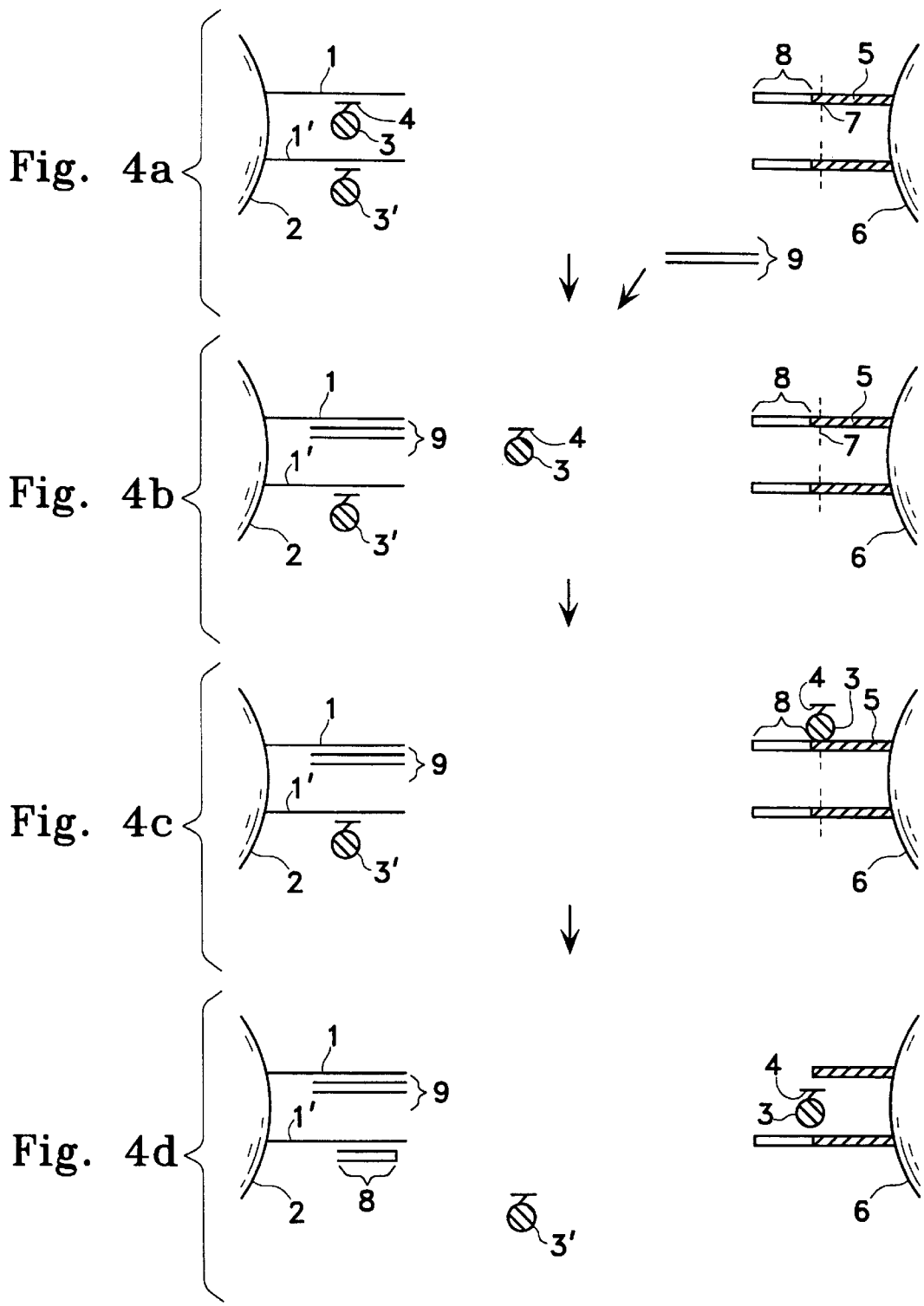

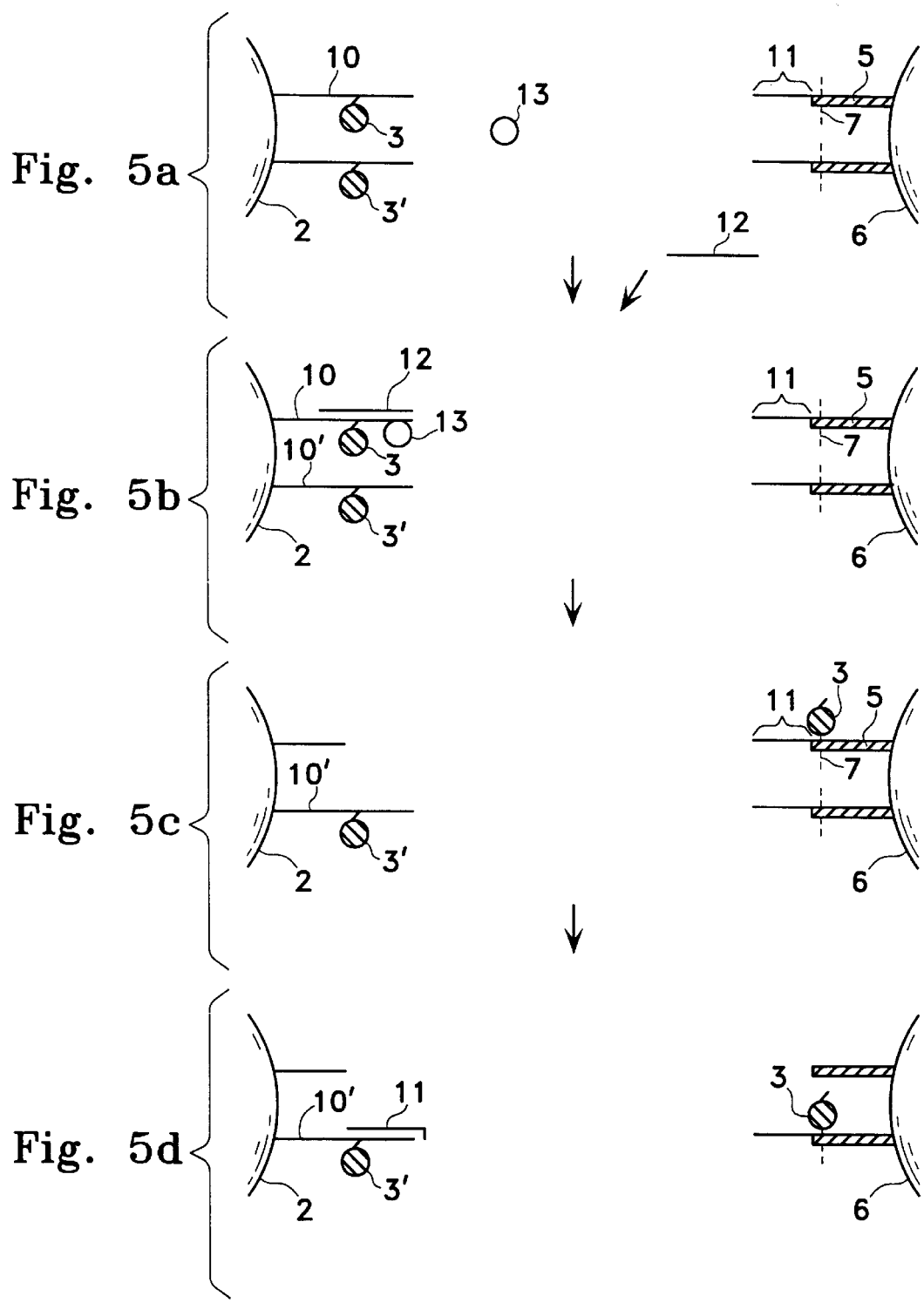

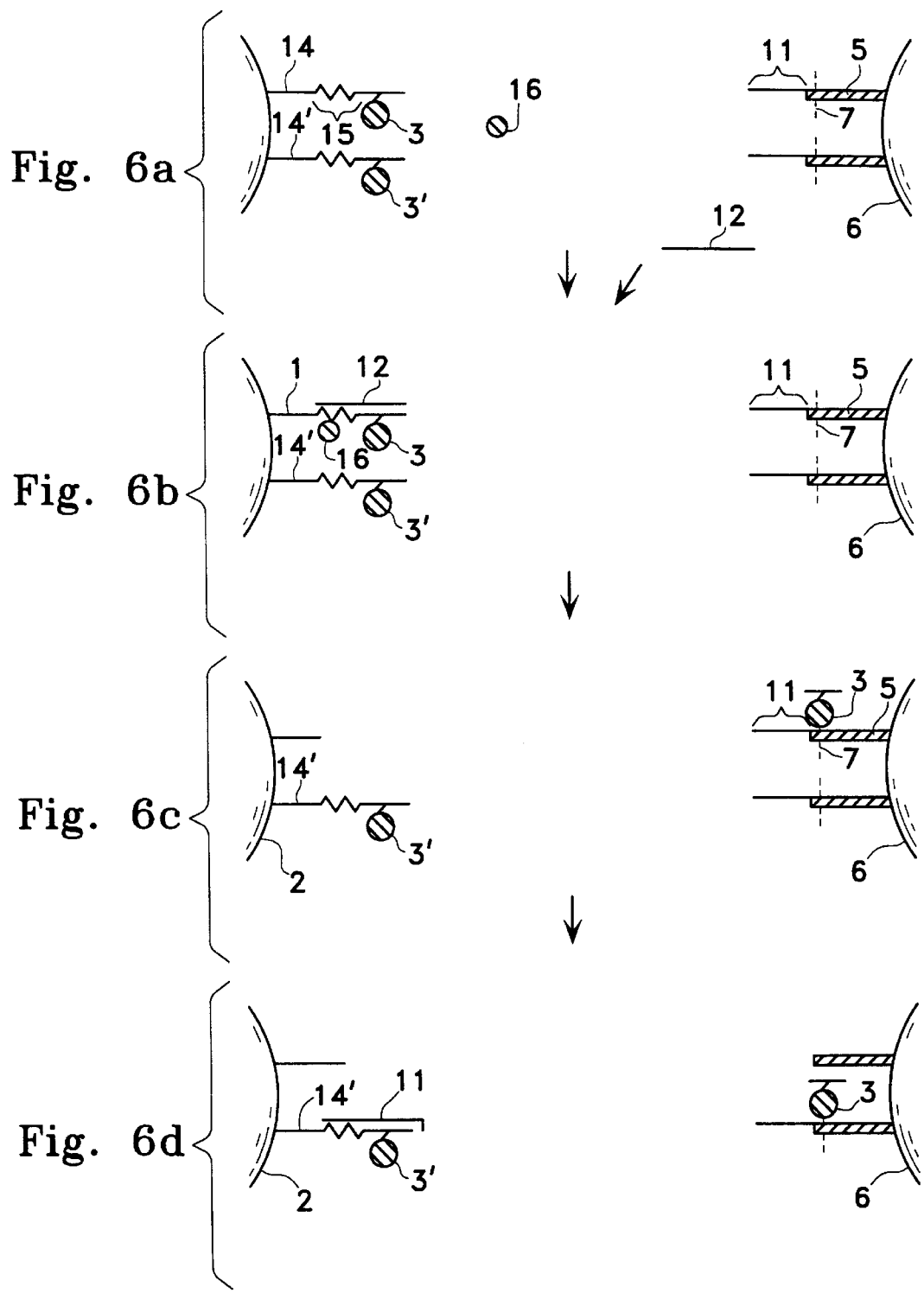

HOMOGENEOUS DIAGNOSTIC ASSAY METHOD UTILIZING SIMULTANEOUS TARGET AND SIGNAL AMPLIFICATION

CROSS-REFERENCE TO RELATED APPLICATIONS

This application is a continuation-in-part of application Ser. No. 08/692,825 which was filed on Jul. 25, 1996 and now U.S. Pat. No. 5,858,665, and which is incorporated herein by reference.

STATEMENT OF RIGHTS TO INVENTIONS MADE UNDER FEDERALLY SPONSORED RESEARCH

This invention was supported in part by a grant from the National Institute of Standards and Technology, Grant No. 70NANB5H1111. The Government may have certain rights to this invention.

TECHNICAL FIELD

This invention is in the field of nucleic acid-based diagnostic assays. More particularly, it relates to a diagnostic technology which utilizes a target cycling reaction ("TCR") to achieve target amplification, and simultaneous signal amplification. This diagnostic technology is useful in detecting, identifying and quantitating target nucleic acid sequences in a sample.

BACKGROUND ART

Nucleic acid hybridization assays are useful in the detection of particular nucleic acid sequences of interest, also referred to as "target" sequences. These target sequences may be characteristic of a particular disease-associated gene, or they may be specific for various organisms or cell types. Accordingly, detection and identification of a particular target sequence can provide diagnostically significant information.

The ability to detect target nucleic acid sequences in a sample by carrying out a hybridization reaction between a target nucleic acid and a complementary "probe" nucleic acid is the cornerstone of nucleic acid-based diagnostic technologies. These assays can generally be characterized as either "heterogeneous" or "homogeneous". Heterogeneous assays depend on the ability to separate hybridized from non-hybridized nucleic acids. One such assay involves immobilization of either the target or probe nucleic acid on a solid support so that non-hybridized nucleic acids which remain in the liquid phase can be easily separated after completion of the hybridization reaction (Southern, *J. Mol. Biol.*, 98: 503–517 (1975).)

In comparison, homogeneous assays depend on other means for distinguishing between hybridized and non-hybridized nucleic acids. Because homogeneous assays do not require a separation step, they are generally considered to be more desirable. One such homogeneous assay relies on the use of a label attached to a probe nucleic acid that is only capable of generating signal when the target is hybridized to the probe (Nelson, et al., *Nonisotopic DNA Probe Techniques*, Academic Press, New York, N.Y., pages 274–310 (1992).)

One of the most significant obstacles to the development of nucleic acid-based diagnostic assays has historically been a lack of sensitivity. In particular, when the number of copies of the target nucleic acid in a sample are limited, sensitivity becomes very important. Many strategies have been designed to overcome this obstacle, with variable success. Among the most successful strategies are those that involve either target amplification or signal amplification. Target amplification involves increasing sensitivity by exponentially multiplying the number of copies of target sequences in a sample. Examples of target amplification techniques include the polymerase chain reaction, or "PCR" (Saiki, et al., *Science* 239: 487–491 (1988), and ligase chain reaction, or "LCR" (Wu, et al., *Genomics* 4: 560–569 (1990).)

Another method for increasing sensitivity is by amplifying the detectable signal which is generated by a single target/probe hybridization event. This can be accomplished by utilizing branched probes, each being capable of generating multiple detectable signals (Urdea, et al, *Clin. Chem.* 39: 725–726 (1993)), or by utilizing cycling probe technology, or "CPT", which relies on the ability to generate multiple detectable probes from a single target sequence (Bekkaoui, et al., *BioTechniques*, 20: 240–248 (1996).)

Still another method for increasing the sensitivity of nucleic acid-based diagnostics employs a cascade reaction to amplify signal. Libeskind (U.S. Pat. No. 4,699,876) discloses a heterogeneous assay utilizing a probe with an enzyme activator attached thereto. Once the probe binds to the target and unhybridized probe is removed, the enzyme activator is used to initiate a signal generation cascade which produces amplified signal levels.

The present invention provides for a homogeneous assay which employs a target cycling reaction, or "TCR", to provide for target amplification. This reaction involves the use of a target analog to mimic the presence of target nucleic acid in a sample. When coupled with a simultaneous signal amplification reaction, the present invention exhibits substantially enhanced sensitivity.

DISCLOSURE OF THE INVENTION

A method for increasing the sensitivity of a nucleic acid hybridization assay which involves a cyclic two-stage reaction called a "target cycling reaction", or "TCR" is disclosed. The first stage of the reaction involves providing a probe-activator complex in an assay system that causes the activator to be released into the assay medium upon hybridization of the target with the probe. The second stage of the reaction involves providing a target analog-anchor complex in the assay system that is cleavable by the activator to cause both the target analog to be released into the assay medium, and the initiation of signal generation from a signal generator. The released target analog can then hybridize to a second probe, which reinitiates the cyclic reaction.

The assay system is designed to prevent the complexed activator from cleaving the target analog-anchor complex, as well as to prevent the complexed target analog from hybridizing with the probe. Accordingly, in one variation of the present invention, the assay system involves attaching the probe-activator complex to one solid surface, and attaching the target analog-anchor complex to another solid surface which is sufficiently distant from the first solid support to prevent cleavage of the target analog-anchor complex by complexed activator. In another variation of the present invention, the assay system involves separating the probe-activator complex from the target analog-anchor complex by a membrane system that is permeable to free activator and free target analog, but impermeable to the complexes.

The assay system of the present invention is designed such that the activator is released only after hybridization of the target (or target analog) to the probe. Accordingly, in one variation of the present invention, the activator is directly attached to the probe, and the complex is designed to release the activator via endonucleolytic or exonucleolytic cleavage of the probe after hybridization with the target (or the target analog.) When a portion of the probe is RNA, RNase H can be used to cleave the probe thus destabilizing the portion of the probe to which the activator is attached. This serves to release the activator into the assay medium, along with whatever portion of the probe remains attached to the activator after RNase H cleavage. Alternatively, restriction endonucleases can be used to effectuate activator release if the probe-activator complex is designed to provide a substrate for cleavage after hybridization of the target (or target analog) which results in activator release.

In another variation of the present invention, the activator is indirectly attached to the probe via direct attachment of the activator to a reporter nucleic acid, which in turn hybridizes to the probe. This combined probe-reporter-activator complex is also referred to herein as a "probe-activator complex." When the activator is indirectly attached to the probe via a reporter nucleic acid, the probe-activator complex is designed to cause destabilization and thus release of the activator (which is usually released while still attached to the reporter) upon hybridization of the target (or target analog) with the probe. This mechanism can be used to detect a double-stranded target nucleic acid, which displaces the reporter nucleic acid via triple helix formation with the probe nucleic acid, or to detect a single-stranded target nucleic acid, which forms a more stable hybrid with the probe than the reporter nucleic acid.

Another aspect of the present invention is the choice of anchor molecule, which effectuates both release of the target analog and generation of signal upon cleavage by the activator. In one variation of the present invention, the anchor is an inactive protein, which can be activated upon cleavage by a protease activator. Signal can be generated after cleavage by including a signal generator in the assay medium that is a substrate for the cleaved (i.e. activated) anchor protein. Such a mechanism for signal generation is referred to as "indirect," because the cleavage reaction itself does not generate signal. A preferred combination of inactive protein and corresponding protease is trypsinogen and enterokinase.

In another variation of the present invention, the anchor is a polysaccharide which is a substrate for an activator that cleaves between individual sugar moieties. These individual sugar moieties can then serve as a substrate for another enzyme included in the assay medium which is capable of catalyzing a signal generation reaction with the appropriate substrates and other assay components. Such a method for generating signal is referred to as a "cascade" which is a form of indirect signal generation that involves at least two additional coupled chemical reactions in addition to the cleavage reaction between the activator and the polysaccharide anchor.

In yet another variation of the present invention, the anchor is a nucleic acid which, when complexed with at least one target analog, provides a substrate for an endonuclease enzyme. Such a target analog-anchor complex can be designed to have signal generators attached thereto which generate signal upon cleavage by the activator, i.e. "direct" signal generation, or via indirect signal generation. In addition, the target analog-anchor complex can be designed to contain more than one target analog, each of which are released into the assay medium upon cleavage by the activator.

The present invention also includes an assay system for determining the presence of a target nucleic acid in a sample suspected of containing the target nucleic acid, which includes the following components:

(a) an assay medium;

(b) a probe nucleic acid-activator complex that has a probe nucleic acid sequence which is complementary to the target nucleic acid sequence, wherein the activator is capable of being released from this complex into the assay medium upon hybridization of the probe and the target;

(c) a target analog nucleic acid-anchor complex that has a target analog nucleic acid sequence which is complementary to the probe nucleic acid sequence, wherein the target analog nucleic acid-anchor complex is capable of being cleaved by the released activator, which results in release of the target analog from the target analog nucleic acid-anchor complex into the assay medium; and (d) a signal generator capable of generating detectable signal in the presence of the cleaved target analog nucleic acid-anchor complex.

The present invention also includes a reagent composition for increasing the sensitivity of a nucleic acid hybridization assay between a probe nucleic acid, and a target nucleic acid having a target nucleic acid sequence, which consists of:

(a) an assay medium;

(b) a probe nucleic acid-activator complex that has a probe nucleic acid sequence which is substantially complementary to the target nucleic acid sequence, and wherein the activator is capable of being released from the probe nucleic acid-activator complex into the assay medium after hybridization of the probe nucleic acid with the target nucleic acid; and (c) a target analog-anchor complex that has a target analog nucleic acid sequence which is homologous to the target nucleic acid sequence, and wherein the target analog-anchor complex is capable of being cleaved by the released activator in such a manner that the target analog is released into the assay medium.

BRIEF DESCRIPTION OF THE DRAWINGS

FIG. 4 illustrates an assay format used to detect a double-stranded target nucleic acid which involves indirect attachment of an activator to a probe via a reporter nucleic acid which hybridizes to the probe.

FIG. 5 illustrates an assay format used to detect a single-stranded target nucleic acid which involves direct attachment of the activator to an RNA probe, and digestion of the probe by RNase H to effectuate activator release.

FIG. 6 illustrates an assay format used to detect a single-stranded target nucleic acid which involves direct attachment to the 5' DNA region of a 5'-DNA:RNA:DNA-3' chimeric probe, and digestion of the RNA region by RNase H to effectuate activator release.

MODES FOR CARRYING OUT THE INVENTION

Figure 1:
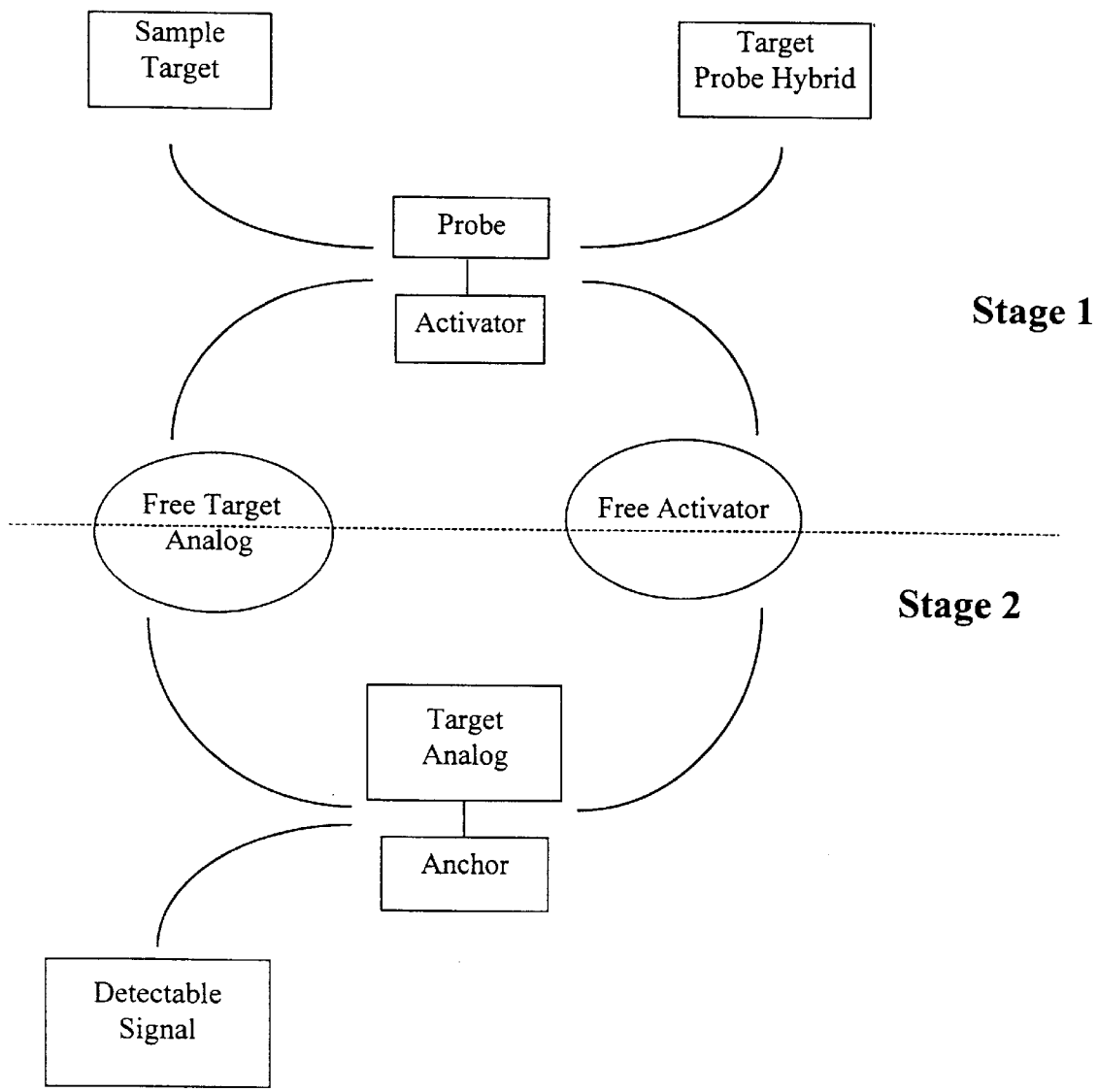
FIG. 1 illustrates a flow diagram of the two-stage target cycling reaction of the assay system of the present invention.

The present invention relates to a homogeneous nucleic acid-based diagnostic assay which utilizes a target cycling reaction to improve sensitivity. In order to more clearly describe the subject matter of the present invention, certain terms used herein shall be defined as follows unless otherwise indicated:

Activator: "Activator" means a molecule that directly or indirectly effectuates a reaction that generates detectable signal from a signal generator, and also acts as a cutting agent to release target analog from the anchor molecule or from the solid surface to which the target analog is attached. The phrase "capable of being released" in reference to a particular activator means that the probe-activator complex is such that in the presence of target (or target analog) under specified conditions, the activator is released into the assay medium (i.e. it becomes "released" or "free" activator).

Anchor: "Anchor" means a molecule to which target analog is attached.

Cascade: "Cascade" means a sequence of coupled reactions, such that the product of a first reaction serves as the catalyst for a subsequent reaction. "Cascade amplification" occurs when the product of the first reaction catalyzes multiple subsequent reactions.

Cleavage Site: "Cleavage site" means a location in (a) a nucleic acid that is susceptible to hydrolysis of at least one native or modified phosphodiester bond in the sugar-phosphate backbone of the nucleic acid; (b) a protein that is susceptible to hydrolysis of a peptide bond in the amino acid backbone; or (c) a polysaccharide that is susceptible to hydrolysis of a glycosidic bond between saccharide subunits.

Cleave: "Cleave" means: (1) to cause a break in the linkage between individual repeating units of a polymer such as a nucleic acid, protein or polysaccharide, using a cutting agent, which results in the production of at least two individual fragments of the polymer, or (2) to cause a break in the linkage between a polymer (i.e. an anchor) and a target analog. The phrase "capable of being cleaved" in reference to a particular cutting agent (such as free activator) means that the linkage between the individual repeating units of the polymer, or the linkage between the polymer and the target analog is such that, in the presence of the cutting agent under specified conditions, the linkage is broken. For example, the linkage between a target analog and an anchor is "capable of being cleaved" by an activator, and cleavage results in release of the target analog into the assay medium (i.e. it becomes "released" or "free" target analog).

Complementary: "Complementary" means the sequence of a nucleic acid of a given polarity which enables it to hybridize with another nucleic acid of opposite polarity based on Watson-Crick base pairing. "Complementary" intends sequences in which all of the bases form base pairs (perfectly complementary) and sequences in which not all of the bases form base pairs, but the complementary nucleic acids are still capable of hybridizing to form a stable duplex (substantially complementary.)

Cutting Agent: "Cutting agent" means a molecule that effectuates a break at a cleavage site. For example, a nuclease cleaves a nucleic acid; a protease cleaves a protein; and amylase cleaves selected polysaccharides.

Digestion: "Digestion" means the degradation of a polymer (e.g. a nucleic acid, protein or polysaccharide) into its individual units (e.g. nucleotides, amino acids or monosaccharides) which is referred to as "complete digestion," or into short segments, i.e. "partial digestion."

Functional Group: "Functional group" means a chemical group or moiety which is capable of reacting with another chemical group or moiety to form a covalent bond, such as a carboxyl group which is capable of reacting with an amine group.

Homogeneous Assay: "Homogeneous assay" means an assay that can be performed without a step to separate unhybridized nucleic acid from hybridized nucleic acid.

Homologous. "Homologous" means that the sequence of one nucleic acid is identical to or essentially the same as (i.e. capable of hybridizing with the same nucleic acids as) another nucleic acid.

Hybridization: "Hybridization" means the formation of a duplex between complementary nucleic acid sequences.

Nucleic Acid Sequence: "Nucleic acid sequence" (or "sequence") means both a nucleic acid having a given sequence of nucleotides, and also the sequence or order of nucleotide bases in the nucleic acid.

Polarity: "Polarity" means the orientation of a nucleic acid which is created when the C3 position of one deoxyribose (or ribose) moiety is linked together with the C5 of the adjacent deoxyribose (or ribose) moiety via a native or modified phosphodiester linkage to create two ends, one with a free C3 (the "3' end") and the other with a free C5 (the "5' end").

Probe: "Probe" means a nucleic acid having a sequence which is complementary to a target nucleic acid sequence.

Probe-Activator Complex: "Probe-activator complex" means a complex of a probe and an activator molecule, and includes a complex formed by direct covalent attachment of an activator to a probe, as well as a complex formed by indirect attachment of an activator to a probe via direct covalent attachment of the activator to a reporter nucleic acid which hybridizes to the probe. The probe-activator complex may also be formed via direct or indirect non-covalent attachment.

Reporter: "Reporter" means a molecule to which activator is attached, and which hybridizes with a probe.

Restriction Endonuclease Cleavage Site: "Restriction endonuclease cleavage site" means the cleavable linkage within or adjacent to a restriction endonuclease recognition sequence.

Restriction Endonuclease Recognition Sequence: "Restriction endonuclease recognition sequence" means a sequence of nucleotides that is specifically recognized by a restriction endonuclease which binds to the sequence and causes cleavage.

Sample. "Sample" means the material being assayed.

Sample Purification. "Sample purification" means isolation and separation of nucleic acids from the non-nucleic acid components of a sample.

Signal: A physical or chemical property, such as chemilluminescence, fluorescence or color, which can be detected and measured, either qualitatively or quantitatively.

Signal Generator: A molecule capable of producing detectable signal after undergoing a chemical reaction. The phrase "capable of generating detectable signal" means that, in the presence of free activator and the stage 2 assay components under specified conditions, the signal generator generates detectable signal.

Spacer Arm: "Spacer arm" means a generally linear chemical moiety, which in the unbound state is bifunctional (i.e., has the same or different functional groups at each end), and which is used to covalently link two molecules together while maintaining a desirable amount of distance between them.

Stable Hybrid: "Stable hybrid" means a duplex of two strands of nucleic acid formed by Watson and Crick base pairing which, under specified conditions, does not have a tendency to become single-stranded.

Target: "Target" means a nucleic acid in a sample having a particular sequence, the presence, absence and/or quantity of which is sought to be determined in an assay.

Target Analog: "Target analog" means a nucleic acid which is provided as one of the assay components and is capable of hybridizing with a probe nucleic acid under assay conditions.

Target Cycling: "Target cycling" means the ability of hybridization of a target nucleic acid to a probe nucleic acid to initiate a cascade which results in release of a target analog nucleic acid, which reinitiates the cascade. See FIG. 1.

Zymogen: "Zymogen" means a substantially inactive protein precursor of an active protein, such as an enzyme.

The present invention relates to a two-stage target cycling reaction assay system for the detection of target nucleic acids. More specifically, the present invention is a two-stage assay system which involves physical separation of the complexed, but not the free, assay components in the reaction. See FIG. 1. The two stages are described as follows:

Stage 1: Single- or double-stranded target nucleic acid present in a sample (or free target analog) reacts with a probe nucleic acid. If the target nucleic acid is complementary to the probe nucleic acid, specific hybridization occurs and triggers the release of the activator ("free activator") into the liquid medium. "Stage 1 components" refers to the assay components which are necessary to cause activator release in the presence of target. This includes a probe-or reporter-activator complex, as well as any additional free assay components which are necessary to effectuate activator release.

Stage 2: The activator effectuates the release of the target analog nucleic acid ("free target analog") into the liquid medium, and also directly or indirectly generates detectable signal from a signal generator. "Signal amplification" can be accomplished by coupling this reaction with a signal generation system that allows the generation of multiple detectable signals from the release of a single target analog. The free target analog nucleic acid provides for "target amplification" by mimicking the presence of target nucleic acid in the sample, and starting the reaction over (i.e., cycling) beginning with stage 1. "Stage 2 assay components" refers to the assay components which are necessary to cause target analog release and signal generation, in the presence of free activator. This includes the target analog-anchor complex and the signal generator as well as any additional free assay components necessary to effectuate target analog release and signal generation.

Figure 2:
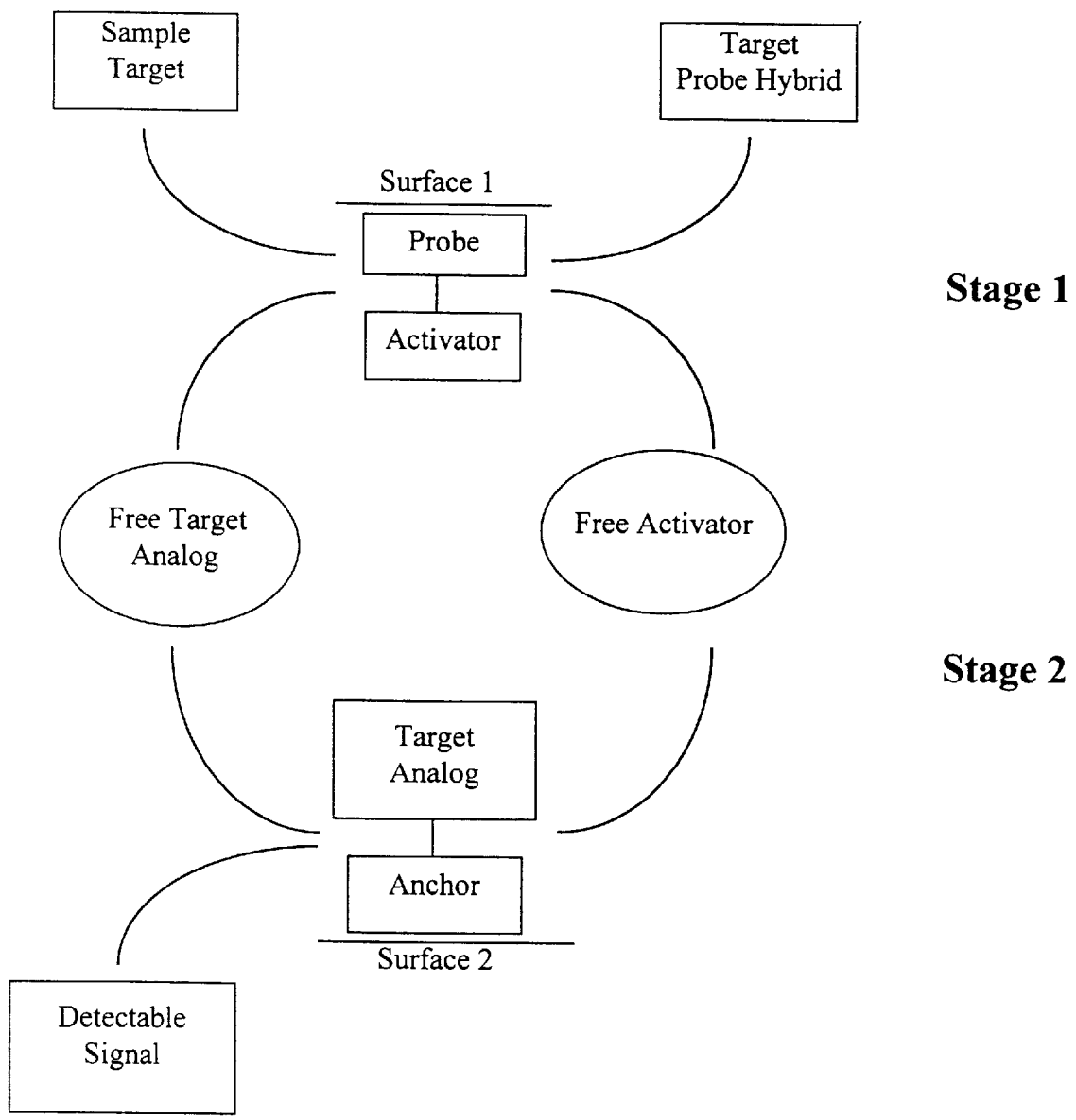
FIG. 2 illustrates a flow diagram of the target cycling reaction of the assay system of the present invention which involves separation of stage 1 and stage 2 complexed assay components by attaching the complexes to different solid supports.
Figure 3:
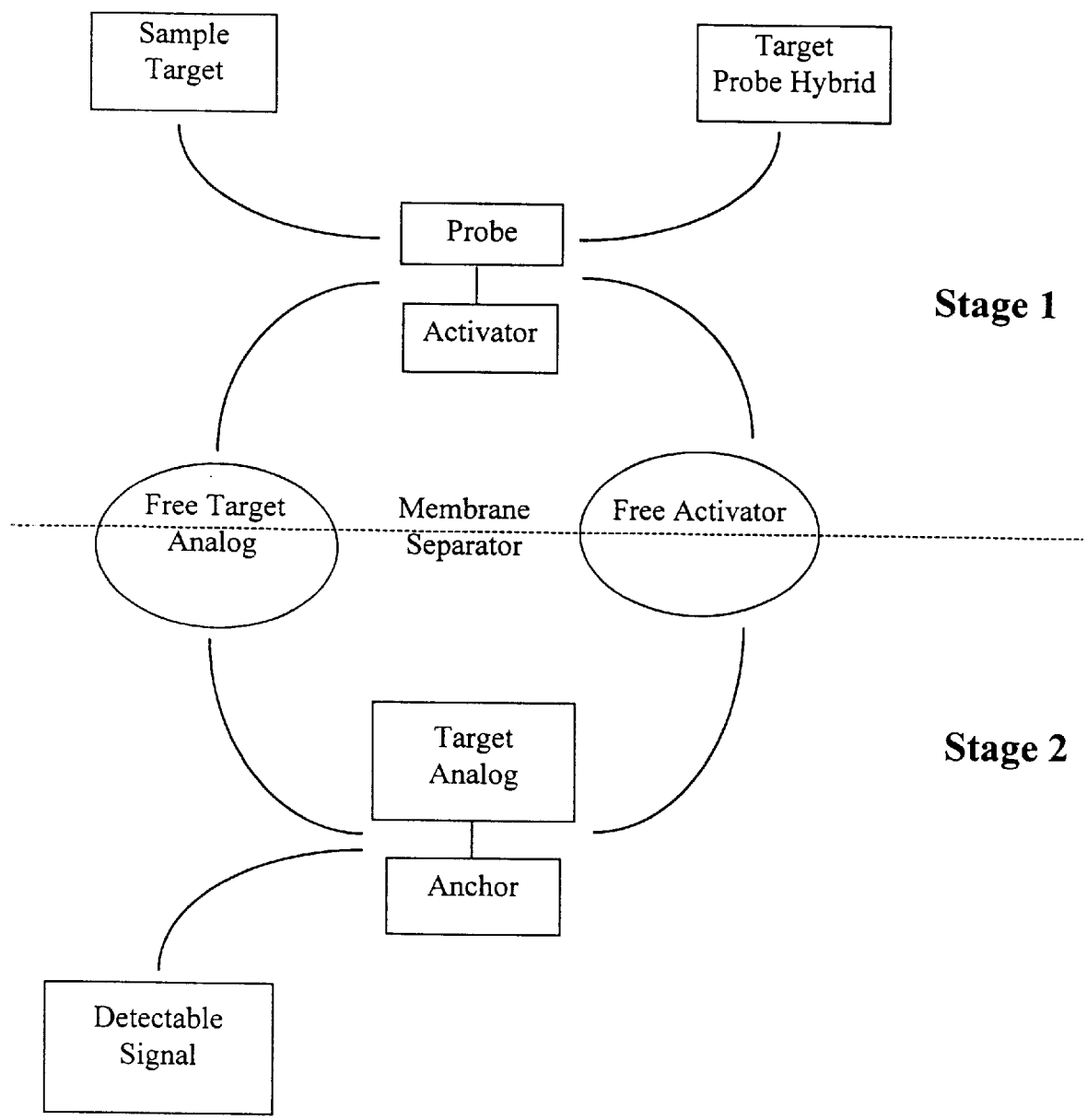
FIG. 3 illustrates a flow diagram of the target cycling reaction of the assay system of the present invention which involves separation of stage 1 and stage 2 complexed assay components using a membrane which is permeable only to free assay components.

The stage 1 and stage 2 reactions can be separated by attaching the complexed stage 1 components, which includes the activator to a different solid support than the complexed stage 2 components, which includes the target analog as depicted in FIG. 2. Alternatively, the stage 1 and stage 2 components can be separated by means of a membrane which is permeable to free, but not complexed, assay components, as depicted in FIG. 3.

Accordingly, the present assay system can be used to simultaneously accomplish both signal and target amplification, which greatly improves assay sensitivity. This added sensitivity can eliminate the need for separate target amplification reactions such as PCR, and makes the assay particularly well-suited for applications where the concentration of target in the sample is minimal, such as would be expected for the amount of pathogen-associated nucleic acids in the early stages of an infectious disease.

The method of the present invention is useful for detecting the presence of a nucleic acid having a particular sequence in a sample (the "target nucleic acid".) The target nucleic acid may be associated with a genetic disease, such as cystic fibrosis or fragile X chromosome, in which case the assay could be used to indicate a predisposition for this disease or to confirm a diagnosis of the disease. Alternatively, the present method may also be used for detecting the presence of organisms associated with pathogenicity, such as mycoplasma, yeast, bacteria and viruses. In addition, it may be used to detect the presence of cancer-associated nucleic acid sequences, such as oncogenes. The present invention may also be used to monitor the sensitivity of different organisms or cell types to treatments, or to detect antibiotic resistance traits in organisms when these traits are associated with particular nucleic acid sequences. In a laboratory setting, the present invention may also be useful to confirm the presence of a particular target nucleic acid sequence, or to test for hybridization of a target nucleic acid sequence prepared in the laboratory with a complementary probe nucleic acid sequence.

Target Nucleic Acid

The target nucleic acid sequence will generally be chosen such that it is characteristic of, or associated with, a particular organism, cell type or gene. Accordingly, detection of the target nucleic acid in the sample would implicate a particular organism, cell type or gene as the source of the target nucleic acid. Selection of the appropriate target nucleic acid sequence would necessarily depend on the goal to be achieved by performing the assay. For example, if the sample was a biological fluid suspected of containing a particular group of organism (kingdom, phylum, family, genus or species), a target nucleic acid sequence would be chosen which was specific for this group of organism.

Many target nucleic acid sequences are known and would be suitable for detection using the method of the present invention. They include sequences that are characteristic of pathogenic bacteria and viruses, as well as sequences associated with tumor-specific antigens and mutant alleles. For example, sequences have been described that serve as targets for the detection of *Mycobacterium kansasii*. (U.S. Pat. Nos. 5,500,341; and 5,518,884). Other target sequences that are characteristic of different mycobacterial species have also been described. (U.S. Pat. Nos. 5,494,796; 5,500,341; and 5,470,723). The spacer region between the 16S and 23S rRNA genes of *Neisseria gonorrhoeae* has served as a target sequence for specific detection this pathogen. (U.S. Pat. No. 5,536,638). Among the viral nucleic acids that serve as target sequences and are thus useful in the detection of these organisms are canine herpesviruses GB and GC, and herpes simplex virus. (U.S. Pat. Nos. 5,529,780; and 5,508,168). Tumors and tumor metastases can be monitored by detecting genes encoding tumor-associated antigens. A nucleic acid sequence that was associated with neoplastic disease and thus was targeted in a probe-based assay was a gene encoding an abnormal tyrosine phosphatase. (U.S. Pat. No. 5,536,636). Genes encoding bladder tumors associated antigens have also been targeted. (U.S. Pat. Nos. 5,512,444; and 5,462,871). Detection of mutant alleles can allow predictions of a disease course or of propensity toward a given disease. A mutant allele associated with Huntington's disease has been targeted in probe-based assays, as has the APC gene associated with certain colorectal cancers. (U.S. Pat. Nos. 5,534,438; and 5,352,775). In other cases, nucleic acid sequences in genes that have undergone deletions have served as the targets for probe-based assays. (U.S. Pat. Nos. 5,532,108; and 5,527,676).

Using the diagnostic method of the present invention, it is possible to detect the presence of a particular target nucleic acid sequence in a sample. Conversely, it is also possible to determine that a particular target sequence is absent. If a target sequence is detected, it is also possible to identify the target sequence based on its ability to hybridize with the particular probe nucleic acid being used. In turn, this enables the identification of a particular cell type, organism, or gene sequence with which the target sequence is specifically associated. It is also possible to quantify the amount of target sequence present based on the amount of signal generated during the assay. Additionally, if the amount of target sequence per cell or organism is known, it is possible to quantify the number of cells or organisms present in the sample.

Sample

The sample may take a variety of forms, including liquid such as water, whole blood, serum, plasma or urine; or solid such as dust, soil, food, or tissue samples. The nucleic acid in the sample must be made available to contact the probe nucleic acid before any hybridization can occur. This generally necessitates at least partial purification of nucleic acid from other biomolecules, such as proteins, lipids, and other cellular components which may be present in the sample, before carrying out the assay. Methods of purifying nucleic acids from biological and non-biological samples are described in the scientific literature and can easily be selected for use depending on the source of the sample and the desired degree of purity. Many of these methods are commercially available in the form of kits.

Hybridization conditions will also influence the necessity for sample purification. When less stringent hybridization conditions are utilized, a more purified sample preparation is generally needed. When more stringent hybridization conditions are utilized, a less purified sample preparation is needed. The effects of various hybridization conditions have been described in the literature. See, for example, Sambrook, et al., *Molecular Cloning: A Laboratory Manual*, Cold Spring Harbor Laboratory Press, Chapter 11 (2d ed. 1989).

Target nucleic acids can be single- or double-stranded. If the target nucleic acid is initially double-stranded, it can be made single-stranded by known methods such as heating, low ionic strength, high pH (for DNA), etc. The target nucleic acid can also be DNA, RNA or a chimera of DNA and RNA.

When the target nucleic acid is RNA, a cDNA copy of the RNA can be generated using reverse transcriptase and an appropriate primer prior to initiation of the assay. In this embodiment, the probe is designed to be complementary to the cDNA generated with reverse transcriptase.

Target Cycling

A unique feature of the present invention is the employment of a target analog nucleic acid to effectuate target cycling. The target analog is conjugated to an anchor, such that release of an activator upon specific hybridization of the target with the complementary probe (i.e., "target DNA identification") causes the release of the target analog from the anchor ("free target analog"), and also initiates the production of detectable signal. The resultant free target analog then hybridizes with a second probe nucleic acid to effectuate the release of a second activator molecule. These reactions cycle, thus amplifying the amount of signal generated by a signal target nucleic acid molecule. Target cycling can eliminate the necessity for a separate amplification step such as PCR, which is subject to the influences of contaminating non-target nucleic acids.

Probe and Target Analog Preparation

The probe and target analog nucleic acids can be either DNA or RNA. They can be prepared chemically or enzymatically by any known method. Enzymatic synthesis can be achieved in vivo using cloning techniques, or in vitro using appropriate polymerase enzymes and substrates. Chemical synthesis is preferred, and can be performed using any known method, such as the method described by Stec, et al. (*J. Am. Chem. Soc.* 106: 6077–6079 (1984)) using the phosphoramidite method and an automated synthesizer, such as Model 380-B from Applied Biosystems, Inc. (Foster City, Calif.).

The assay of the present invention depends on the ability of target and target analog to hybridize with probe. Once a target nucleic acid sequence has been selected, either from the literature or from isolating and sequencing the target from a source of nucleic acid, the probe and target analogs are designed to have the appropriate nucleic acid sequence. In other words, the nucleic acid sequence of the probe will necessarily be complimentary to the nucleic acid sequence of the target, and the nucleic acid sequence of the target analog will necessarily be complementary to the nucleic acid sequence of the probe.

The length of the probe and target analog nucleic acids will be any length which is sufficient to form specific and stable hybrids with their complementary nucleic acids. For example, the target analog must be sufficiently long and have a sequence which will allow it to form a stable hybrid with the probe, but it is not necessary that it have the same length or sequence as the target nucleic acid. It is also possible that the target analog can have the same sequence and length as the target nucleic acid. The probe nucleic acid must also be of sufficient length and have a sequence which will allow it to form a specific and stable hybrid with both the target and the target analog nucleic acid.

Target Analog-Anchor Complex

An important feature of the present invention is that the target analog remain unavailable to hybridize with the probe until after the presence of target nucleic acid has been detected in the assay system. Thus, the target analog is preferably complexed to an anchor to form a target analog-anchor complex. The anchor consists of a linear polymeric biomolecule, such as an amino acid polymer, a nucleic acid polymer, a polysaccharide, or a synthetic organic polymer whose linkage to the target analog is cleavable by the activator. The target analog is released from the anchor via the cutting action of the activator molecule. A preferred anchor is a protein such as a zymogen, which can be converted from an inactive form to an active form by cleavage at a specific location.

Attachment of nucleic acids to biomolecules such as proteins, polysaccharides and other nucleic acids has been thoroughly described in the scientific literature. The method used to attach the target analog to the anchor should, however, yield a complex that satisfies the following criteria: (1) the complex should be stable in the assay medium in the absence of free activator, and cleavable by free activator to release free target analog; (2) the anchor should be activatable by the activator; (3) the activated anchor should be capable of initiating signal generation; and (4) the free target analog should be capable of hybridizing to probe.

The target analog may also be attached directly to a solid surface. For example, if the complexed activator is inactive (e.g. due to steric hindrance), and an additional stage 2 assay component can be included in the assay medium which can be activated by free, but not by complexed activator. Then, if the free activator also cleaves the linkage between the target analog and the solid surface, a separate anchor is not necessary.

Examples of different anchors include, inter alia, the following:

Protein Anchors

When the anchor is a protein, such as a zymogen, the activator is generally a protease enzyme. Zymogens are inactive enzyme precursors, such as the proteolytic enzymes of the stomach and pancreas (for example, chymotrypsinogen and trypsinogen) and coagulation factors. When a zymogen is used as the anchor, a zymogen activator is used as the activator. Zymogen activators are protease enzymes that cleave an inactive zymogen to convert it into an active protein. Zymogen activators and zymogens can be obtained from natural sources, or they may be synthesized using recombinant DNA techniques. Many activators and zymogens are commercially available. A preferred zymogen-activator pair is trypsinogen-enterokinase.

Zymogens can be susceptible to auto-activation or activation by protease contamination in the sample, which can result in generation of non-specific signal. Addition of commonly available protease inhibitors such as PMSF can be effective in decreasing premature activation of zymogens. Stabilization of the zymogen can also be performed using other known methodologies. One method for stabilizing trypsinogen is covalent attachment of modifying groups such as polyethylene glycol (PEG) or auanidine. Attachment of PEG is referred to herein as pegylation, and attachment of guanidine is referred to as guanidation. It would be straightforward for one skilled in the art to experimentally determine an appropriate method for stabilizing a zymogen of interest using these or other known methods.

A convenient site for attachment of PEG or guanidine to trypsinogen are the ε-amino groups of lysine residues. However, the enterokinase recognition sequence of trypsinogen contains a lysine residue which could be modified by attachment of PEG or guanidine. Trypsinogen modified in this way may not be efficiently cleaved by enterokinase. Since the lysine residue in the enterokinase cleavage site can be replaced by arginine without significantly altering the ability of the trypsinogen to be cleaved by enterokinase, it is desirable to use such an arginine mutant of trypsinogen when trypsinogen is to be modified on the ε-amino groups of lysine. Such mutations may be introduced through known techniques such as site-directed mutatgenesis. Genes mutated in this way can be placed into an appropriate expression vector, transformed into an appropriate host cell, and expressed by the host cell. Mutated zymogen can then be purified from the host cells using methods known in the art prior to being used in the assay.

Certain methods of generating target analog-anchor complexes utilize a cysteine residue in the anchor protein as a site of attachment for a linker arm which is also capable of binding the target analog nucleic acid sequence. It is thus advantageous in one embodiment of the present invention, that the cysteine residue in the zymogen utilized for attachment of this linker be positioned amino-terminal to the activator cleavage site. If there is not a naturally occurring cysteine residue located in this region of the zymogen, then one may be introduced by manipulating the zymogen gene using known techniques such as site-directed mutatgenesis.

An appropriate location for introduction of a cysteine residue into a zymogen, such that it does not interfere with activator cleavage, can be determined experimentally without undue effort. Zymogen mutated in this way can be expressed and purified as described above. Such cysteine mutants of trypsinogen can be used to form target analog-anchor complexes in combination with an appropriate linker such as NHS-PEG-maleimide (Shearwater Polymers, Inc., Huntsville, Ala.) and a thiol-modified target analog nucleic acid. As used herein, the term "cysteine zymogen mutant" is used to refer to a modified zymogen having at least one cysteine amino acid residue which is amino-terminal to the activator recognition sequence.

In one embodiment of the present invention, a modified zymogen may be used which contains both types of mutations described above, namely an amino-terminal cysteine mutation and a lysine to arginine substitution mutation in the protease cleavage recognition site.

Examples of zymogens with their respective active proteins and corresponding zymogen activators are given below in Table I.

TABLE I

| Activator | Zymogen | Active Protein |
| --- | --- | --- |
| enterokinase acid proteases from Aspergillus sp. | trypsinogen | trypsin |
| trypsin | chymotrypsinogen | chymotrypsin |
| trypsin | proelastase | elastase |
| trypsin | proproteinase E | proteinase E |
| trypsin | procarboxypeptidase A | carboxypeptidase A |
| trypsin | procarboxypeptidase B | carboxypeptidase B |
| trypsin | procolipase | colipase |
| trypsin | prophospholipase | phospholipase |
| factor XIIa | prekallikrein | kallikrein |
| plasminogen activator | plasminogen | plasmin |
| thrombin | fibrinogen | fibrin |
| coagulation factor Xa | prothrombin | thrombin |
| kallikrein | plasminogen proactivator | plasminogen activator |
| factor XIIa | coagulation factor XI | coagulation factor XIa |
| coagulation factor IXa | coagulation factor X | coagulation factor Xa |
| kallikrein | coagulation factor XII | coagulation factor XIIa |
| thrombin | coagulation factor XII | coagulation factor XIIIa |

It is also possible to generate mutated zymogens that contain alternative activator cleavage sites for use in the assay. For example, when mutations are made in trypsinogen which introduce a chymotrypsin cleavage site in place of the naturally occurring enterokinase cleavage site, then chymotrypsin is used as the activator in an assay where the mutated trypsinogen is the zymogen anchor. This embodiment has the advantage of being less costly, since chymotrypsin is less expensive than enterokinase. One skilled in the art could easily generate a variety of mutated zymogens that have alternative activators.

Polysaccharide Anchors

When the anchor is a polysaccharide, an activator is used that is capable of cleaving the linkage between sugar moieties. This accomplishes release of the target analog into the assay medium, and in the presence of other assay medium components, simultaneous release of individual sugar moieties.

For example, amylose can be used as an anchor, which consists of individual glucose moieties linked together in the form of a linear polymer. amylase can then be used as an activator, which cleaves the bond between glucose moieties at several locations in the polymer. If one end of the amylose is attached to the target analog, and the other end is attached to a solid support, the amylose anchor will not contain any terminal glucose moieties, which will only be produced upon cleavage by amylase. This allows a second enzyme, amyloglycosidase, to be included in the assay medium, which will rapidly cause the release individual glucose moieties from the terminal ends of the amylase cleavage product. Free glucose can then be detected by including glucose oxidase in the assay medium which converts glucose to gluconate and hydrogen peroxide. Hydrogen peroxide reacts with many known signal generators to cause detectable signal to be formed. Many other reactions and reaction cascades are known in the art which involve signal generation via polysaccharide cleavage.

Nucleic Acid Anchors

When the anchor is a nucleic acid polymer, it is possible to combine the target analog and the anchor into one nucleic acid molecule. By incorporating a restriction endonuclease recognition sequence into this molecule, a restriction endonuclease can be used as the activator to effectuate release of the target analog. One advantage of the use of a nucleic acid anchor is that no conjugation is necessary between the target analog and the anchor, which can both be synthesized simultaneously. It is also possible to combine together multiple target analog sequences to the anchor so that the activator can cleave between individual target analog, as well as cleaving between the target analog and the anchor. When the anchor is a nucleic acid and the activator is a restriction endonuclease, the anchor is preferably double stranded. The restriction endonuclease is chosen such that it will effectuate cleavage of the target analog-anchor complex at a specific location to release the target analog(s). Many different restriction endonucleases have been described. Listed below in Table II are exemplary restriction endonucleases and their corresponding recognition sequences:

TABLE II

| Endonuclease | Sequence ID No. | Recognition Sequence* |
|---|---|---|
| AccI | SEQ ID NO: 1 | GT/MKAC |
| AcyI | SEQ ID NO: 2 | GR/CGYC |
| AhaIII | SEQ ID NO: 3 | TTT/AAA |
| BalI | SEQ ID NO: 4 | TGG/CCA |
| BbvI | SEQ ID NO: 5 | GCAAGCNNNNNNNN/ |
| BbvI | SEQ ID NO: 6 | CGTCGNNNNNNNNNNNN/ |
| BglI | SEQ ID NO: 7 | GCCNNNN/NGGC |
| BstXI | SEQ ID NO: 8 | CCANNNNN/NTGG |
| CauII | SEQ ID NO: 9 | CC/SGG |
| Eco47III | SEQ ID NO: 10 | AGC/GCT |
| EcoA | SEQ ID NO: 11 | GAGNNNNNNNGTCA |
| EcoB | SEQ ID NO: 12 | TGANNNNNNNNTGCT |
| EcoDXI | SEQ ID NO: 13 | ATCANNNNNNNATTC |
| Eco105I | SEQ ID NO: 14 | TAC/GTA |
| EcoNI | SEQ ID NO: 15 | CCTNN/NNNAGG |
| EcoRV | SEQ ID NO: 16 | GAT/AGC |
| Fnu4HI | SEQ ID NO: 17 | GC/NGC |
| FokI | SEQ ID NO: 18 | GGATGNNNNNNNNN/ |
| HaeI | SEQ ID NO: 19 | WGG/CCW |
| HgaI | SEQ ID NO: 20 | GACGCNNNNNNNNNN/ |
| HindII | SEQ ID NO: 21 | GTY/RAC |
| HpaI | SEQ ID NO: 22 | GTT/AAC |
| MstI | SEQ ID NO: 23 | TGC/GCA |
| NaeI | SEQ ID NO: 24 | GCC/GGC |
| NarI | SEQ ID NO: 25 | GG/CGCC |
| NruI | SEQ ID NO: 26 | TCG/CGA |
| NspBII | SEQ ID NO: 27 | CMG/CKG |
| PvuII | SEQ ID NO: 28 | CAG/CTG |
| RsaI | SEQ ID NO: 29 | GT/AC |
| ScaI | SEQ ID NO: 30 | AGT/ACT |
| SfiI | SEQ ID NO: 31 | GGCCNNNN/NGGCC |
| SmaI | SEQ ID NO: 32 | CCC/GGG |
| SnaBI | SEQ ID NO: 33 | TAC/GTA |
| StuI | SEQ ID NO: 34 | AGG/CCT |

TABLE II-continued

| Endonuclease | Sequence ID No. | Recognition Sequence* |
|---|---|---|
| Tth111-I | SEQ ID NO: 35 | GACN/NNGTC |
| XmnI | SEQ ID NO: 36 | GAANN/NNTTC |

*A = Adenine, T = Thymine, C = Cytosine, G = Guanine, N = Any Nucleotide, M = A, C; W = A, T; R = A, G; K = G, T; S = G, C; and Y = C, T.

Probe-and Reporter-Activator Complex

The activator can be attached directly to the probe nucleic acid to form a probe-activator complex, or alternatively, the activator can be attached indirectly to the probe by attaching it to a reporter nucleic acid to form a reporter-activator complex which hybridizes with the probe nucleic acid. (Reporter nucleic acids can be prepared as described above for probe nucleic acids.)

Attachment of the activator to the probe nucleic acid or the reporter nucleic acid can be accomplished by any known biomolecular conjugation technique, and may involve covalent or high-affinity non-covalent interactions. By "high-affinity", it is meant that the association of activator and probe/reporter nucleic acid is adequately stable to prevent premature activator release. The choice of probe, activator and conjugation method should, however, yield a complex that satisfies the following criteria: (1) the complex should be stable in the assay medium (and if the complex is a reporter-activator complex, the probe-reporter hybrid must also be stable in the assay medium) in the absence of target (and free target analog) nucleic acid; (2) the target (and free target analog) nucleic acid should be capable of effectuating release of the activator; and (3) the free activator should be capable of activating the anchor.

The structure and use of spacer arms coupled to nucleic acids for the attachment of proteins or other substituents are well known in the literature. Generally, the spacer arm will have two functional groups attached at either end, one of which will be used to attach the spacer arm to the nucleic acid, and the other of which will be used to attach the spacer arm to the activator. These functional groups may be the same (i.e. homobifunctional) or different (i.e. heterobifunctional.) Examples of homobifunctional reagents include; glutaric dialdehyde, disuccinimidyl-suberate, phenylene diisothiocyanates, bis-nitrophenol esters, and bis-azido compounds. Examples of heterobifunctional reagents include; 2-acetamido-4-mercaptobutyric acid hydrazide ("AMBH"), succinimidyl-3-(2-pyridylthio) propionate ("SPDP"), N-succinimidyl-maleimido compounds, N-succinimidyl-iodoacetate, p-nitrophenyl 6-maleimidocaproate, and 4-chloroacetylphenylmaleimide. (Wong, S. S., Chemistry of Protein Conjugation and Cross-Linking, CRC Press, Boca Raton, 1991; Hermanson G. T., Bioconjugate Techniques, Academic Press, New York, 1995.)

Functionally activated synthetic polymers such as polyethylene glycol are particularly well suited for use as linkers. The synthetic polymer is preferably hydrophilic and water soluble, or it can be rendered water soluble by incorporating oxygen (or less frequently nitrogen) atoms which would thus be available for forming hydrogen bonds in aqueous solution. Synthetic hydrophilic polymers for use in the present invention include, inter alia, activated forms of polyethylene glycol (PEG), polyoxyethylene, polyvinyl pyrrolidones, polymethylene glycol, polytrimethylene glycol, and derivatives and copolymers thereof. Many difunctionally activated polymers have previously been described. See, for example, U.S. Pat. No. 5,565,519, which describes crosslinking protein via PEG derivatives, and which can easily be adapted for use in the present invention by using a difunctionally activated polymer and selective attachments involving the use of blocking groups to prevent undesired linkages.

The site of attachment of the activator to the probe or reporter nucleic acid (either directly or via a spacer arm) can be at any position (i.e., to any of the nucleotides), so long as attachment of the activator does not substantially diminish the ability of the probe nucleic acid to hybridize with the target nucleic acid, or the reporter nucleic acid to hybridize to the probe nucleic acid. Preferably, the site of attachment is at or near the 3' or 5' end of the nucleic acid.

Alternatively, the activator may be attached directly to the probe or reporter nucleic acid via a "tail" or "hairpin" structure in the probe or reporter nucleic acid that is designed to minimize any steric effects of the activator molecule on the hybridization reaction involving the nucleic acid to which it is attached.

One non-covalent method for attaching the probe or reporter to the activator makes use of the high-affinity interaction between biotin and streptavidin. The probe or reporter nucleic acid and the activator can each be labeled with biotin according to one of several methods known in the art. Addition of streptavidin to such biotinylated components will induce formation of a probe-activator or reporter-activator complex via a biotin-streptavidin-biotin bridge. Other non-covalent attachments involving different high-affinity ligand-receptor binding interactions are also within the present invention.

The methods described herein for formation of probe-activator complexes can be easily adapted for generation of target analog-anchor complexes in embodiments where the anchor is a protein.

Assay Format and Activator Release

The effectiveness of the present assay depends on the ability to bring about release of the activator into the liquid medium (which initiates the target cycling reaction) upon hybridization of a target nucleic acid with its complementary probe nucleic acid. Several different mechanisms can be employed to release activator upon hybridization of the target (or target analog) nucleic acid with the probe.

For example, detection of double-stranded target nucleic acid may involve release of an activator-reporter nucleic acid complex from a triple-stranded target-probe hybrid. Alternatively detection of single-stranded target nucleic acid may involve the use of exonuclease-mediated release of activator via partial or total digestion of the probe nucleic acid to which the activator is attached. In another embodiment, detection of single-stranded target nucleic acid involves endonuclease-mediated release of activator via endonucleolytic cleavage of the probe nucleic acid to cause activator release. In yet another embodiment, detection of a single-stranded target may involve the use of strand displacement mechanisms to cause release of a reporter-activator complex from the probe in the presence of target nucleic acid.

An assay for detecting double-stranded target is depicted in FIG. 4. In part (a) of the figure, the stage 1 assay components are shown to consist of the following: the probe (1) is attached to a first solid surface (2). The activator (3) is attached to a reporter nucleic acid (4) to form a "reporter-activator complex", which hybridizes to the probe (1). The stage 2 assay components are shown to consist of the following: the anchor (5) is attached to a second solid surface (6). The anchor contains at least one cleavage site (7), which can be cleaved by the activator (3). At least one strand of the double-stranded target analog (8) is attached to the anchor (5).

Part (b) of the figure shows the results of addition of target (9), which forms a triple helix between the target (9) and the probe (1). This causes the reporter-probe hybrid to be destabilized, which results in release of the reporter-activator complex from the probe (1) and thus the solid surface (2), into the assay medium. In part (c), the reporter-activator complex is shown to have migrated through the assay medium until it recognizes and binds to its cleavage site (7). (After cleavage, the reporter-activator complex can continue cleaving additional anchor molecules.) In part (d), cleavage of the anchor (5) at cleavage site (7) is shown to have resulted in release of the double-stranded target analog (8) into the assay medium, which then migrates through the assay medium until it hybridizes to a second probe (1'), thus effectuating release of a second activator (3'). These individual reactions cycle, until all of the target analog or reporter present in the assay system has been released, whichever is the limiting component.

When the activator is attached directly to the probe nucleic acid, release of the activator into the liquid medium may be effectuated by degradation of the probe nucleic acid after hybridization to the target nucleic acid. For example, when the target nucleic acid is single-stranded DNA and the probe nucleic acid is RNA, activator release can be achieved by inclusion of RNase H in the assay medium, which will selectively cleave the RNA strand of a DNA:RNA hybrid. This assay format is depicted in FIG. 5. In part (a) of the figure, the stage 1 assay components are shown to consist of the following: the probe (10) is attached to a first solid surface (2). The activator (3) is attached to the probe (10) thus forming a "probe-activator complex." The stage 2 assay components consist of the following: the anchor (5) is attached to a second solid surface (6). The anchor contains at least one cleavage site (7), which can be cleaved by the activator (3). The single-stranded target analog (11) is attached to the anchor (5).

Part (b) of FIG. 5 shows the result of addition of single-stranded DNA target (12), which forms a probe-target hybrid. The RNA probe in this hybrid is a substrate for the RNase H (13). In part (c), the RNase H (13) is shown to have digested the probe (10), thus releasing the activator (3), which migrates through the assay medium until it recognizes and binds to cleavage site (7). (After cleavage, the activator (3) can continue cleaving additional anchor molecules.) In part (d), cleavage of the anchor (5) at cleavage site (7) is shown to release the single-stranded target analog (11) into the assay medium, which hybridizes to a second probe (10'), thus effectuating release of a second activator (3'). These reactions cycle until all of the target analog or reporter present in the assay system has been released, whichever is the limiting component. This mechanism for activator release has the added advantage of releasing the target nucleic acid from the sample back into the liquid medium for subsequent binding to another probe nucleic acid, thus reinitiating the reaction.

A variation of the assay as described for FIG. 5 utilizes a DNA probe, and a DNA exonuclease to effectuate digestion of the probe. This requires the probe to be designed, such that hybridization between the probe nucleic acid and the target nucleic acid, provides a 5' end on the probe nucleic acid which is susceptible to exonucleolytic cleavage by a 5'-3' exonuclease enzyme, such as Taq polymerase or *E. coli* DNA polymerase I (Sambrook et al., *Molecular Cloning, A Laboratory Manual, Second Edition,* Cold Spring Harbor Laboratory Press, pages 5.50 & 5.38 (2d ed. 1989)). Alternatively, the probe could be designed such that when the probe nucleic acid hybridizes to the target nucleic acid, the 3' end of the probe nucleic acid is susceptible to exonucleolytic cleavage by a 3'-5' exonuclease enzyme, such as exonuclease III (Sambrook et al., *Molecular Cloning, A Laboratory Manual, Second Edition*, Cold Spring Harbor Laboratory Press, page 5.84 (2d ed. 1989)).

In a preferred embodiment, the assay system utilizes a chimeric probe, which consists of three separate regions: a 3' DNA region attached to a solid support, a 5' DNA region to which the activator is attached, and an intervening region of RNA. This assay format is depicted in FIG. 6. In part (a), the stage 1 assay components are shown to consist of the following: the chimeric probe (14) is shown with its RNA region (15) flanked by a DNA region on either side (not numbered.) The DNA region which is in the 3' direction from the RNA region (14) is attached to a first solid surface (2), and the activator (3) is attached to the DNA region which is in the 5' direction from the RNA region. Free RNase H (16) is included in the assay medium and participates in the stage 1 reaction as described below. The stage 2 assay components are as described for FIG. 5.

Part (b) of FIG. 6 shows the result of addition of single-stranded target (12), which forms a probe-target hybrid. The RNA region (15) of this hybrid is a substrate for the RNase H (16). In part (c), the RNase H (16) is shown to have digested the RNA region (15) in the chimeric probe (14), thus destabilizing the hybrid between the target (12) and the DNA region of the probe which was 5' to the RNA region to which the activator is attached, which causes this DNA region and the attached activator (3) to be released into the assay medium. The activator (3) migrates through the assay medium until it recognizes and binds to cleavage site (7). (After cleavage, the activator (3) can continue cleaving additional anchor molecules.) Part (d) is as described for FIG. 5.

It is also possible to design the probe-target hybrid to provide sites for specific cleavage of either or both strand(s) using restriction endonucleases or mechanisms involving cleavage at mismatch sites to destabilize the hybrid enough to cause release of the activator into the liquid medium. In addition, a probe can be designed which forms a sequence-dependent hairpin structure when hybridized with the target (or target analog.) This hairpin structure can be recognized and cleaved by certain endonucleases (such as Cleavase®, Third Wave Technologies, Inc., Madison, Wis.) By attaching the activator to the appropriate position on the probe, cleavage can effectuate activator release.

Signal Generation

The way in which signal is generated in the assay system depends on the type of activator-anchor system chosen. For example, signal can be generated in the following manner: (1) cleavage of the anchor by the activator may result in the anchor being changed (i.e., activated) such that it can generate signal only after cleavage (i.e., "indirect signal production," which involves at least one additional reaction besides cleavage); (2) cleavage of the anchor alone may generate signal (i.e., "direct signal production"); and (3) cleavage of the anchor may convert it to a catalyst of or a substrate for a second reaction, the products of which participate in a third reaction, and so on (i.e., a "signal producing cascade," which is a form of indirect signal generation involving multiple coupled reactions). "Signal amplification" stems from the fact that each activator molecule released into the assay medium is capable of causing, either directly or indirectly, multiple signal generators to exhibit detectable signal.

It is also possible for signal to be generated in an assay system that involves direct attachment of the target analog to a solid surface. In this assay format, rather than generating signal via activation of an anchor, signal is generated via activation of an additional stage 2 assay component which is free in the assay medium but which can only be activated by free activator, and not by complexed activator. For example, if the target analog is linked to a solid surface via a linkage which can be cleaved by free activator, and a stage 2 assay component is included in the assay system which can be activated via cleavage by the activator, an "activatable" anchor is unnecessary.

Many different methods for generating signal from the hydrolysis of biomolecules are well known in the art and can easily be adapted for use in the assay systems of the present invention. The following examples are illustrative of the various combinations of activators, anchors and mechanisms for generating signal.

Protease Activator and Zymogen Anchor

When the anchor is a zymogen, the activator converts the zymogen into its corresponding active protein. This active protein catalyzes a chemical reaction with the signal generator to produce detectable signal. The end product of such a reaction can be a fluorescing entity, a chemilluminescent entity, or a colored entity. This is an example of "indirect signal generation."

Examples of signal generator-active protein combinations are given below in Table III.

TABLE III

| Active protein | Signal Generator | Reference |
| --- | --- | --- |
| Carboxypeptidase A | Z-Gly-Phe-OH | Bachem BioScience* |
| Carboxypeptidase B | Bz-Ala-Arg-OH.HCl | Bachem Bioscience |
| Chymotrypsin | Bz-DL-Phe-b-naphthyl ester | Bachem Bioscience |
| Collagenase | Z-Pro-Ala-Gly-Pro4MbNA (SEQ ID NO: 37) | Bachem Bioscience |
| Kallikreins | Z-Tyr-ONp | Bachem Bioscience |
| Renin | Z-Pro-Phe-His-Leu-Leu-Val-Tyr-Ser-pNA (SEQ ID NO: 38) | Bachem Bioscience |
| Thrombin | Z-Lys-SBzl.HCl | Bachem Bioscience |
| Trypsin | Z-Arg-AMC.HCl | Bachem Bioscience |
| Trypsin | Z-Arg-pNA.HCl | Bachem Bioscience |
| Trypsin | Z-Gly-Gly-Arg-pNA-HCl | Bachem BioScience |
| Trypsin | Z-Lys-Onp.HCl | Bachem BioScience |
| Trypsin | Na-CBZ-L-Arg-7 Amido-4-Methyl-Coumarin | Sigma** |
| Trypsin | Na-CBZ-L-Arg-p-NA | Sigma |
| Plasmin | D-Val-L-Leu-L-Lys-pNA | Kabi Diagnostica*** |

*Feinchemikalien, Switzerland
**St. Louis, Missouri
***Sweden

Endonuclease Activator and Nucleic Acid Anchor

When the anchor is a nucleic acid polymer, signal generators can be incorporated into the polymer such that the activator cleaves the anchor to release the target analog into the liquid medium and simultaneously generates signal. This is an example of direct signal production.

The signal generator in this case will typically be a fluorophore (fluorophore 1), which is conjugated in defined proximity to a quencher (fluorophore 2), having spectral properties (excitation/emission profiles) which inhibit the fluorescence generated by fluorophore 1, thus eliminating the inherent presence of a fluorescent signal. Conjugation of the fluorophores to the anchor is carried out such that cleavage by the activator will result in spatial separation of the fluorophores, which results in signal generation. By incorporating multiple fluorophore pairs in the same anchor molecule, each of which generate signal upon cleavage by the activator, the signal can be "amplified." The incorporation of known fluorophores into oligonucleotides has been reported (Stevens et al., *Clinical Chemistry,* 41:1683 (1995).) The conjugation of a fluorophore to an oligonucleotide can be achieved by known methods.

An indirect method of signal generation used in combination with a nucleic acid anchor requires labeling of the nucleotides within the anchor using known methods, for example by incorporation of radioactive elements or attachment of a fluorescent chromophore or biotin. A 5'-3' and/or 3'-5' exonuclease enzyme is then used to release individual labeled nucleotides into the assay medium. The assay medium is then physically separated from undigested target analog-anchor complexes, and the amount of label in the medium is quantitated using a standard method appropriate for the label used.

Amylase Activator and Amylose Anchor

When the anchor is a polysaccharide (such as amylose) and the activator is capable of cleaving the glucosidic linkages, (such as amylase), individual glucose molecules can be released into the assay medium from the anchor polysaccharide via cleavage by amyloglycosidase. By also including glucose oxidase in the assay medium, hydrogen peroxide will be formed from glucose. The hydrogen peroxide in turn generates detectable signal from the signal generator. This is an example of indirect signal generation which involves a signal producing cascade.

Detection of hydrogen peroxide can easily be accomplished using peroxidase, and commercially available signal generators. The following substrates are preferred (Sigma Chemical Company, St. Louis, Mo.): 2,2'-azino-bis(3-ethylbenzthiazone-6 sulfonic acid (ABTS), o-phenylenediamine (OPD), 3,3',5,5'-tetramethylbenzidine (TMB), and o-dianisidine 5-aminosalicylic acid (SAS).

Target Quantitation

The amount of target present in a sample can be quantitated by comparing the amount of signal generated in the assay system to standard curves. Known amounts of target are added to the assay system and time vs. signal intensity curves are plotted at different target concentrations using a kinetic mode of measurement. The assay is then performed on a sample having an unknown amount of target present and the amounts of target is determined by comparison to the standard curves. Alternatively, a value of signal at a fixed time point "T" can be determined for known amounts of target, and used to quantitate the amounts of target in a signal from the amount of signal generated at this same time point.

Separation of Stage 1 from Stage 2 Complexed Components

The method of the present inventions is performed in an "assay system", i.e. an assay compartment or vehicle which contains the physical means for separating stage 1 from stage 2 assay components.

It is important that the assay system provides for physical separation of the probe-activator complex (or the reporter-activator complex which is hybridized to the probe) and the target analog-anchor complex. See FIG. 1. In this manner, the target analog-anchor complex will not be cleaved and signal will not be generated until the activator is released subsequent to hybridization of the target nucleic acid (or target analog nucleic acid) with the probe nucleic acid. Otherwise, non-specific anchor cleavage and signal generation would occur and result in a false positive result.

Separation of the stage 1 from stage 2 complexed assay components can be achieved in a solid-support system by attaching the probe-activator complex (or the probe to which a reporter-activator complex is hybridized) to one surface, and the target-anchor complex to another surface as depicted in FIG. 2. Alternatively, the stage 1 and stage 2 complexed assay components can be separated by a membrane which is specially designed to separate the complexed assay components from their corresponding free forms, as depicted in FIG. 3. When such a membrane is utilized, it may be desirable to couple both the anchor and the probe to a membrane impermeable macromolecule in order to facilitate separation by the membrane.

Examples of solid support materials are, for example, nitrocellulose, polystyrene, nylon, glass, silica or polymethacrylate. Examples of permeable membrane materials are, for example, cellulose, derivatized cellulose (nitrocellulose, cellulose-acetate), and nylon. The choice of separation mechanism can easily be made based on the characteristics (size, molecular weight, etc.) of the complexed assay components to be separated. Many known examples of appropriate solid support systems and membrane systems are known in the relevant art.

Attachment of the probe (either before or after it is complexed with the activator or hybridized to the reporter-activator complex) and/or the anchor (either before or after attachment of the target analog) can be performed using known techniques. Attachment can be covalent or ionic, but is preferably covalent. Ionic attachment can be accomplished by binding the negatively charged nucleic acid probe to a positively charged surface, such as nitrocellulose or nylon (Gingeras, et al., *Nucleic Acids Res.* 15: 5373–5390 (1987).) Covalent attachments of nucleic acids to solid supporters are described in Bioconjugate Techniques, Hermanson, et al., Academic Press, New York, New York, page 55 (1990).

Covalent attachment of the probe to a solid support generally involves modification of the probe at either the 5' or 3' terminus. Terminal modification is preferred in order to lessen interference with target (and target analog) hybridization to the probe. For example, the 5' terminus can be modified by introducing reactive amine moieties (using an automated synthesizer) which can then be used in a coupling reaction with activated supports. Examples of other methods of attachment involve carbodiimide based attachment of nucleic acids to cellulose, sephadex or sephacryl; and immobilization of the nucleic acid via the nucleic acid bases which are coupled to the solid support, and vice versa (Lund, et al., *Nucl. Acids Res.* 16: 10861–10880(1988).)

It is also possible to use a glass or plastic assay compartment as one surface, and a microsphere placed inside the glass assay compartment as the second surface. Both surfaces can then be activated using known methods, and used as a platform for attachment of the target analog anchor complex to one surface, and the probe to the other surface.

The assay system can be dry until addition of a liquid sample, or a liquid medium can be supplied and added either before, during or after sample addition.

EXAMPLES

The following series of examples describes various embodiments of the assay method of the present invention. Examples 1–7 describe one embodiment which involves the use of an immobilized probe nucleic acid-activator complex, and a zymogen anchor-target analog complex. Examples 8 and 10 describe two different methods for stabilization of the zymogen trypsinogen which involve a chemical modification of trypsinogen. Examples 9–11 describe an alternative method for generating an immobilized target analog-anchor complex that contains stabilized trypsinogen. Two alternative examples for generation of a probe-activator complex, one utilizing covalent attachment methods (Example 12) and one utilizing non-covalent attachment methods (Example 13) are also provided. The final example (Example 14) describes the generation of certain cysteine mutants of trypsinogen that are useful for generating target analog-anchor complexes in one embodiment of the present invention.

Example 1

Attachment of Enterokinase to a Probe Nucleic Acid to Form a Probe-Activator Complex Enterokinase is a serine protease that effectuates cleavage of trypsinogen to trypsin. Enterokinase is highly specific for the amino terminal sequence of trypsinogen, Val-Asp-Asp-Asp-Asp-Lys- (SEQ ID NO:39), which is released as a hexapeptide in the activation process by cleavage between the Lys and the Ile (Yamashina, et al., *Biochim. Biophys. Acta*, 20: 433–434 (1956). Enterokinase is conjugated to the 3' end of an oligonucleotide probe to form a probe-activator complex as follows:

The probe nucleic acid is an oligonucleotide having a sequence which is complementary to the target nucleic acid, which has been activated to contain a thio group in the 3' end nucleotide. By starting with such a 3' activated oligonucleotide, complex formation using this method is independent of size and sequence, and can be used to conjugate a probe nucleic acid of any size or sequence to enterokinase without hindering the ability of the probe oligonucleotide to hybridize with a complementary target nucleic acid.

The probe is prepared as a 3'-DNA:RNA:DNA-5' chimera having 25 to 40 deoxyribonucleotides in each DNA segment, and 10 to 20 ribonucleotides in the RNA segment.

The 3' activated probe nucleic acid is prepared using known techniques. For example, a 3' end amine modified oligonucleotide can be prepared using an automated synthesizer, then activated to contain sulfhydryls (i.e., "thiolation") using known methods. See, for example, Bioconjugate Techniques, Hermanson, et al., Academic Press, New York, page 662–664 (1996).

Enterokinase is modified using SPDP, which contains N-hydroxyl succinimide ("NHS") ester on one end, and which creates an amide bond with the amino group on the enterokinase. This modified enterokinase is activated to contain pyridisulfide groups for coupling to the sulfhydryls in the modified oligonucleotide. The activated enterokinase is then reacted with the activated oligonucleotide. The coupling reaction forms disulfide bonds between the oligonucleotide and the enterokinase.

The individual steps involved in complex formation are further described as follows:

(a) Activation of the Oligonucleotide Probe
1. Dissolve the 3' amine modified oligonucleotide to be thiolated in 250 µl of 50 mM sodium phosphate, pH 7.5.
2. Dissolve SPDP to make a 20 mM concentration in DMSO.
3. Add 50 µl of the SPDP solution to the oligonucleotide solution and mix well.
4. React for 1 hour at room temperature.
5. Remove excess reagents by gel filtration.
6. Add 20 µl of 1M dithiothreitol ("DTT") and incubate at room temperature for 15 minutes to release the pyridine-2-thione group and form the free sulfhydryl.
7. Purify the thiolated oligonucleotide from excess DTT by gel filtration.

(b) Activation of Enterokinase
1. Dissolve enterokinase at a concentration of 10 mg/ml in 50 mM sodium phosphate, 0.15M NaCl, pH 7.2.
2. Dissolve SPDP to make a 20 mM concentration in DMSO.
3. Add 25 µl of the SPDP solution to each ml of the enterokinase solution to be activated and mix well.
4. React for 30 min. at room temperature.
5. Purify using gel filtration in 50 mM sodium phosphate, 0.15M NaCl, 10 mM EDTA, pH 7.2.

(c) Conjugation of Activated Oligonucleotide and Activated Enterokinase
1. Dissolve the activated oligonucleotide in water or 10 mM EDTA at a concentration of 0.05–25 µg/ml.
2. Add the activated oligonucleotide solution to the activated enterokinase in a 10 fold molar excess.
3. React at room temperature with gentle mixing.
4. Purify the conjugate by gel filtration using centrifugal concentrators.

Example 2

Attachment of the Probe-Enterokinase Complex to a Solid Support

The probe is immobilized via carbodiimide (EDC) mediated attachment of the 5' phosphate of the DNA:RNA:DNA chimeric probe to beads which contain reactive surface carboxyls (Bangs Laboratories, Carmel, Ind.) according to the method described by Lund, et al. *Nucl. Acids Res.* 16: 10861–10880 (1988). Carbodiimide reacts with the 5' phosphate group to form a phosphoramidate, which is then reacted with the carboxyl- containing beads to form a covalent bond between the oligonucleotide and the bead. (Hermanson, Nucleic Acid and Oligonucleotide Modification and Conjugation, Bioconjugate Techniques, Academic Press, pages 649–651) (1995).)

Example 3

Testing for Efficacy of the Immobilized Probe-Enterokinase Complex

The efficacy of the immobilized probe-enterokinase complex prepared as described in Example 2 is determined by performing the following two tests using known techniques:

(a) Test for Enterokinase
1. Add free target analog to assay buffer (100 mM Tris, 1 mM $Ca^{2+}$, pH 8.0) in a sufficient quantity to effectuate hybridization with the probe. Also add 5'-3' exonuclease (2.5 units per µg of DNA).
2. Add the solution prepared in step 1 to the immobilized probe-enterokinase complex.
3. Incubate under conditions which allow hybridization to occur.
4. Remove the assay buffer.
5. Test for enterokinase released into the assay buffer by performing an assay for conversion of trypsinogen to trypsin.

(b) Test for Enterokinase Activity
1. Add free target analog to assay buffer (100 mM Tris, 1 mM $Ca^{2+}$, pH 8.0) in a sufficient quantity to effectuate hybridization with the probe. Also add 5'-3' exonuclease (2.5 units per µg of DNA).

2. Add the solution prepared in step 1 to the immobilized probe-enterokinase complex.
3. Incubate under conditions which allow hybridization to occur.
4. Remove the assay buffer.
5. Add the assay buffer containing free enterokinase to immobilized target analog-trypsinogen complex prepared as described below in Example 5, and test for signal generation as described below in Example 6, part (c).

Example 4

Attachment of Trypsinogen to a Solid Support

Trypsinogen is an inactive form of the enzyme trypsin, which is activated by cleavage with enterokinase. Trypsinogen is a 221 amino acid polypeptide, which has several tyrosine residues which are distal to the N terminal end of the molecule. Trypsinogen is coupled to a solid support by conjugating the phenolic side chain in the tyrosine moiety to a diazonium activated matrix on the solid support. The solid support is commercially available modified polystyrene microsphere (Bangs Laboratories, Carmel, Ind.), which are diazonium activated by acid treatment, followed by reaction with $NaNO_2$.

The individual steps involved in complex formation are further described as follows:

(a) Activation of the Solid Support
1. Wash the beads in 2.5 volumes of coupling buffer (0.1M sodium borate, pH 9.5)
2. Centrifuge (for 1.5 ml microfuge tube, 14,000 rpm, 5 minutes)
3. Resuspend in 2.5 volumes of ice cold 2N HCl
4. Centrifuge, and resuspend three times
5. Resuspend in 2 volumes of HCl
6. Add 0.25 volume $NaNO_2$ (50 mg/ml in cold water), and mix gently at 4° C. for 15 minutes.

(b) Attachment of Trypsinogen
1. Wash the activated beads with 2.5 vol. of a 1:1 mixture of coupling buffer and 2N HCl
2. Centrifuge and decant
3. Add trypsinogen solution (7.5 mg/ml in coupling buffer)
4. React overnight at 4° C. while mixing gently
5. Wash the conjugated beads with 3 volumes of coupling buffer, 0.05% Triton X100 (EM Sciences, Gibbstown, N.J.)
6. Centrifuge and decant
7. Wash and equilibrate with assay buffer (100 mM Tris, 1 mM $Ca^{2+}$, pH 8.0)

Example 5

Attachment of Target Analog Nucleic Acid to Immobilized Trypsinogen

The target analog is prepared with a nucleic acid sequence which is complementary to the probe, and binds to the probe.

Trypsinogen is first modified by selective protection of the lysine ε-amino groups, followed by specific modification of the N-terminal a-amino group and subsequent deprotection as described by Magee, et al. *Biochem J.* 197: 239–244 (1981).

The individual steps involved in complex formation are further described as follows:

(a) Trypsinogen Purification through CM-Cellulose Chromatography
1. Dissolve 500 mg trypsinogen in 50 ml citric acid/NaOH buffer (0.01M, pH 3.7) and load onto a 100 ml bed of CM-cellulose pre-equilibrated in the same buffer.
2. Elute with a linear gradient of citric acid/NaOH buffer (10–250 mM, pH 3.7)
3. Dialyze the cationic trypsinogen against HCl (1 mM), and freeze dry.

(b) Acetimidate Protection of ε-Amino Lysine
1. Dissolve 100 mg cationic trypsinogen in 100 ml $CaCl_2$ solution (0.05M) at room temperature, and adjust the pH to 9.5 with NaOH
2. Add 220 mg methyl acetimidate, and maintain the pH at 9.5. Add 5 more portions of 220 mg methyl acetimidate at 20 min. intervals. After 3 hr. titrate the pH to 9.5 with HCl (1 mM), and freeze dry.
3. Dissolve the product in 10 ml boric acid/NaOH buffer (0.1M, pH 8.5) and add acetic anhydride in 2 ml acetonitrile. Stir at room temperature for 1 hour, and dialyze against HCl (1 mM) with several changes, then freeze dry.
4. Dissolve the product in 5 ml of aqueous ammonia (specific gravity 0.88):acetic acid (15:1, v/v), pH 11.3, and stir for 6 hr.
5. Add 50 ml $CaCl_2$ Solution (0.02M), freeze dry and redissolve in 50 ml water, and freeze dry again
6. Dissolve the product in 20 ml citric acid/NaOH (0.01M, pH 3.7), and purify using ion - exchange chromatography on CM cellulose (as described above.) (The extent of the reaction is determined by Fluorescein isothiocyanate (FITC) and picrylsulfonic acid (TNBS))

(c) Conjugation of the Target Analog to the α-amino Group in Trypsinosen
1. A 5' thio-containing target analog is prepared as described in Example 1.
2. The thio group is reacted with the α-amino group as described for Example 1, part (c).

(d) Deprotection of the Lysine ε-Amino Groups
1. The target analog-trypsinogen conjugate is reacted with ammonium hydroxide.

Example 6

Testing for Efficacy of the Immobilized Target Analog-Trypsinogen Complex

The efficacy of the immobilized target analog-trypsinogen complex prepared as described in Example 4 is determined by performing the following three tests using known techniques:

(a) Test for Target Analog Release
1. Add free enterokinase to assay buffer (100 mM Tris, 1 mM $Ca^{2+}$, pH 8.0) in a sufficient quantity to effectuate cleavage of the target analog-anchor complex.
2. Add the solution prepared in step 1 to the immobilized target analog-anchor complex.
3. Incubate under conditions which allow cleavage to occur.
4. Remove the assay buffer.
5. Test for free target analog released into the assay buffer.

(b) Test for Target Analog-Probe Hybridizations
1. Add free enterokinase to assay buffer (100 mM Tris, 1 mM $Ca^{2+}$, pH 8.0) in a sufficient quantity to effectuate cleavage of the target analog-anchor complex.

2. Add the solution prepared in step 1 to the immobilized target analog-anchor complex.
3. Incubate under conditions which allow cleavage to occur.
4. Remove the assay buffer.
5. Add probe to the assay buffer and test for hybridization using known techniques.

(c) Test for Signal Generation

1. Prepare enterokinase solution as described in step 1 in (a) above, and add signal generator (i.e., trypsin substrate).
2. Add the solution prepared in step 1 to the immobilized target analog-anchor complex.
3. Incubate under conditions which allow cleavage to occur.
4. Measure the detectable signal.

Example 7

Assay Performance

The following steps describe the preparation of the assay system and performance of the assay:

(a) Preparation of the Assay Medium

Assay buffer is prepared to contain 100 mM Tris, pH 8.0, and 1 mM $Ca^{2+}$. To the assay buffer is added RNase H (Amersham Life Science, Cleveland, Ohio. The substrate, Z-Gly-Pro-Arg-pNA (Sigma Chemical Co., St. Louis, Mo.) in lyophilized form is added to the assay buffer.

(b) Preparation of the Assay System

Assay medium is added to an assay chamber, along with the beads to which target analog-trypsinogen complex has been covalently attached as described in Example 4, and the beads to which probe-enterokinase has been attached as described in Example 2.

(c) Performance of the Assay

Nucleic acids are purified from the sample using known techniques. An aliquot of the resultant purified nucleic acids from the sample are added to the assay system, and the assay is allowed to equilibrate. Upon target identification (i.e. specific hybridization between target nucleic acid from the sample and the probe), the RNase H cleaves the RNA portion of the probe, causing free enterokinase (along with the DNA portion of the probe to which it is attached) to be released into the assay medium. Enterokinase diffuses through the assay medium, and cleaves trypsinogen to simultaneously release target analog and form trypsin. Trypsin reacts with the substrate to generate signal, which is detected spectrophotometrically at 405 nm. The amount of target nucleic acid present in the sample is quantitated using a kinetic mode of measurement.

Example 8

Stabilization of Trypsinogen by PEGylation

Attachment of polyethylene glycol (PEG) functional groups was used as a method to stabilize trypsinogen.

1. Trypsinogen is dissolved in cold 0.1M borate, pH 8.0.
2. While mixing add NHS-PEG-biotin (Shearwater Polymers Inc., Huntsville, Ala.) to the trypsinogen solution. The ratio of the NHS-PEG-Biotin : trypsinogen can be in the range of 2.5–10.
3. React for at least 4 hours or overnight at 2–8° C.
4. Terminate the reaction via desalting.
5. Purify using ion exchange chromatography.
6. The pegylated trypsinogen can be visualized on an SDS-PAGE gel.
7. Pegylated trypsinogen stored at 2–8° C. was stable for at least two weeks, as indicated by the observation that it had minimal trypsin activity.

Example 9

Immobilization of Free Trypsinogen

Free trypsinogen was attached to a solid support as follows:

1. 1 g carboxyl modified CPG beads (CPG Inc., Lincoln Park, N.J.) were washed twice with 10 ml DMF.
2. 1M carbonyl dimidazole (Sigma Chemical Company, St. Louis, Mo.) was added and the beads were reacted for 1 hour at room temperature with continuous mixing.
3. The beads were washed three times with DMF.
4. 200 mg trypsinogen in 5 ml of 25 mM borate buffer, pH 8 was added.
5. The reaction was carried out for 5 hours at room temperature and then overnight at 2–8° C. with continuous mixing.
6. The beads were then washed several times with 2.5 mM HCl to eliminate the unbound trypsinogen and then stored in 2.5 mM HCl.

Example 10

Stabilization of Trypsinogen by Guanidination

Stabilization of trypsinogen was achieved by another method in which guanidine modifying groups were attached to trypsinogen. The method used is similar to a method described by Mir (*Biochim. Biophys. Acta* 1119 261–267 (1992)):

1. 1 g o-methyl-isourea was dissolved in 5 ml water, the pH adjusted to 10. 5, and volume brought up to 10 ml.
2. The trypsinogen, either in free form or immobilized as described in Example 9, was reacted with the o-methyl-isourea solution at pH 10.5 at a concentration of 10 mg/ml in the final solution.
3. The reaction mixture was incubated at 2–8° C. with constant mixing for 2 days.
4. Following desalting or dialyzing in 25 mM borate, pH 8, the guanidinated trypsinogen was purified until homogeneity by cation exchange chromatography (in the case of free trypsinogen) or by washing the beads (in the case of immobilized trypsinogen).
5. The purified material was stored as it came off the column, in 0.2M NaCl, pH 8.

The resulting guanidinated trypsinogen had the added advantage of being especially well-suited for amino-terminal specific attachment to target analog nucleic acids.

Example 11

Conjugation of DNA to Immobilized-Guanidinated Trypsinogen

The probe DNA was attached to the immobilized trypsinogen as follows in order to generate an immobilized target analog-anchor complex:

1. 100 mg beads containing the immobilized-guanidinated trypsinogen prepared in Example 10 were washed in 0.1M borate buffer, pH 8.

2. 4mg NHS-PEG-maleimide (Shearwater Polymers, Inc., Huntsville, Ala.) crosslinker was added to the beads in 1 ml of 0.1M borate buffer and reacted for 4 hours at room temperature with constant mixing.

3. The beads were washed and 10 nmol SH modified oligonucleotide in 0.1M borate buffer, pH 8 was added and allowed to incubate overnight at 2–8° C. with continuous mixing.

4. Following the reaction the beads were washed and stored in 2.5 mM HCl.

Immobilized guanidinated trypsinogen-target analog complex prepared in this way is now ready for use in the assay of the present invention.

Example 12

Formation of Probe-Activator Complexes

An alternative method for formation of covalently coupled probe-activator complexes was performed as follows with enterokinase as the activator:

(a) Activation of Enterokinase

1. Dissolve 58.4 µl (1 nmol) enterokinase (Biozyme, 2.57 µg/µl stock solution) in 500 µl, 0.1M MES buffer, pH 6.1.

2. Mix 25 µl 0.2M 2-acetamido-4-mercaptobutyric acid hydrazide (AMBH) in DMF with 0.2M 2,2'-dithiodipyridin (DDP) in DMF and add the mixture immediately to the enterokinase solution.

3. Add 60 µl of 10 mM 1-ethyl-3-(3'-dimethylaminopropyl)-carbodiimide (EDAC) in the same MES buffer.

4. Mix overnight at 4° C.

5. Desalt the reaction mixture by applying to a 10/10 Pharmacia column packed with superfine Sephadex G-25. Elute with 0.1M Tris, 1 mM CaCl$_2$, pH 8.0 buffer. Collect the excluded fractions containing the modified protein, EK-AMBH-DDP (usually 1.5 ml).

(b) Activation of the Amino-DNA

1. Dissolve 15 nmole amino-DNA in 150 µl water.

2. Add 300 µl 0.1M borate buffer, pH 8.0.

3. Add 1 mg 3-(2'pyridyl-dithio)-propionic acid N-hydroxy succinimide ester (SPDP) preliminary dissolved in 50 µl DMF 4. Mix at room temperature for 1 h.

5. Desalt the reaction mixture by applying to a 10/10 Pharmacia column packed with superfine Sephadex G-25. Elute with 0.1M Tris, 1 mM CaCl$_2$, pH 8.0 buffer. Collect the excluded fractions containing the SPDP-DNA (usually 1.5 ml).

6. To 0.75 ml SPDP-DNA solution add 10 µl 1M solution of 1,1 -dithiothreitol in water and mix for 2 minutes at room temperature.

7. Desalt the reaction mixture by applying to a 10/10 Pharmacia column packed with superfine Sephadex G-25. Elute with 0.1M Tris, 1 mM CaCl$_2$, pH 8.0 buffer. Collect the excluded fractions containing the SH-DNA (usually 1.5 ml). Use the product immediately for conjugation.

(c) Conjugation

1. Mix the 1.5 ml SH-DNA solution with the 1.5 ml EK-AMBH-DDP solution and shake overnight at 4° C.

2. Apply the reaction mixture to a Pharmacia 5/5 MonoQ column equilibrated with 25 mM Tris, pH 8.0. Elute with a 0 to 100% salt gradient over 25 minutes. The conjugate comes together with the DNA excess. Pool the fractions of this part of the chromatogram which have enterokinase activity (EK-DNA/DNA mixture).

3. Apply 100 µl EK-DNA/DNA mixture to a 10/30 Pharmacia Superose 6 column. Elute with 0.1M Tris, 1 mM CaCl$_2$, pH 8.0. The conjugate comes just before the DNA peak. Pool the fractions having enterokinase activity.

Example 13

Formation of Probe-Activator Complexes Using Non-Covalent Interactions

A method for forming probe-activator complexes using non-covalent interactions is the use of a biotin-streptavidin-biotin bridge. In this embodiment, the probe and the activator are each labeled with biotin, and the addition of streptavidin induces formation of the complex. Two alternative methods for preparation of biotinylated enterokinase are presented while the probe is biotinylated according to methods well-known in the art.

(a) Direct Biotinylation of Enterokinase

1. Dissolve 7 µl enterokinase (Biozyme, 2.57 µg/µl stock solution) in 168 µl PBS.

2. Add 11.9 µl of 1 mM Biotinamidocaproate N-hydroxy succinimide ester in DMSO.

3. Mix at room temperature for 1 h.

4. Desalt the reaction mixture by applying to a 10/10 Pharmacia column packed with superfine Sephadex G-25. Elute with 0.1M Tris, 1 mM CaCl$_2$, pH 8.0 buffer. Collect the excluded fractions containing biotin modified enterokinase together with the unmodified enzyme (usually 1.5 ml).

5. Purify the Biotin-enterokinase by affinity chromatography. This is done via utilizing a commercially available monomeric avidin gel (Pierce Chemicals, Rockford, Ill.). The reaction buffer is 0.1M borate, 0.15M NaCl; pH 7.2. Elution buffer consists of 2 mM biotin in the reaction buffer.

6. Remove free biotin from eluted sample by dialysis or by applying to a 10/10 Pharmacia column packed with superfine Sephadex G-25. Elute with 0.1M borate, 0.15M NaCl; pH 7.2.

(b) Biotinylation of Enterokinase Using a Polyethylene Glycol (PEG) Linker

1. Dissolve 7 µl enterokinase (Biozyme, 2.57 µg/µl stock solution) in 100 µl of 0.1M borate, pH 8.0 buffer.

2. Add 10 µl reagent solution (100 mg/ml Biotin-PEG-N-hydroxy succinimide ester in the same borate buffer).

3. Mix for 1 h. at room temperature

4. Desalt the reaction mixture by applying to a 10/10 Pharmacia column packed with superfine Sephadex G-25. Elute with 0.1M Tris, 1 mM CaCl$_2$, pH 8.0 buffer. Collect the excluded fractions containing biotin-PEG modified enterokinase together with the unmodified enzyme (usually 1.5 ml).

5. Purify the Biotin-PEG-enterokinase by affinity chromatography as described in part (a) of this Example.

(c) Creation of a DNA-Enterokinase Conjugate Via Streptavidin-Biotin Interactions 1. The probe is biotinylated using one of the known standard procedures.

2. The biotinylated probe is allowed to interact with streptavidin so as to saturate all biotin sites with streptavidin.

3. This is followed by incubating the streptavidinated probe with biotinylated enterokinase (prepared as in part a or b of this Example). The incubation is carried out at 37° C. overnight.

This method can be easily adapted for formation of target analog-anchor complexes by non-covalent interactions.

Example 14

Cysteine Mutants of Propeptide Region of Trypsinogen

Several trypsinogen mutants were generated that have cysteine residues which are added amino-terminal to the cleavage recognition site which facilitate the generation of target analog-anchor complexes using certain method (e.g., Example 11). The mutations were introduced using standard PCR-based mutagenesis techniques. A rat anionic trypsinogen clone in the expression vector pTrap was utilized for generation of the mutants (*Biochemistry* 26: 2616–2623 (1987)). The trypsinogen which is purified from host cells transformed with this pTrap vector contains five additional amino acids compared to wild-type. The five amino acids are located immediately amino-terminal to a valine residue that adjacent to the enterokinase cleavage recognition site. Shown below is the amino acid sequence of the amino terminus of trypsinogen purified as described above. The five added amino acids are the first five in the sequence. The underlined residues correspond to the enterokinase cleavage recognition sequence (SEQ ID NO:40):

```
 1   2   3   4   5   6   7   8   9   10  11
Ile Gln Ala Phe Pro Val Asp Asp Asp Asp Lys
```

The cysteine mutations were introduced at the following positions: Ala (position 3), Phe (position 4); Pro (position 5), and Val (position 6). The mutated versions of trypsinogen were expressed in and purified from bacterial cultures. When a cysteine residue was introduced in place of the amino terminal isoleucine residue, the mutant proved to be unstable because the cysteine residue was cleaved off by the host cell after expression. Thus, this amino-terminal position is not an appropriate location for placement of a cysteine residue.

---

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (xi) SEQUENCE DESCRIPTION: SEQ ID NO:1:

GTMKAC                                                                     6

(2) INFORMATION FOR SEQ ID NO:2:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (xi) SEQUENCE DESCRIPTION: SEQ ID NO:2:

GTMKAC                                                                     6

(2) INFORMATION FOR SEQ ID NO:3:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (xi) SEQUENCE DESCRIPTION: SEQ ID NO:3:

TTTAAA                                                                     6

(2) INFORMATION FOR SEQ ID NO:4:

(i) SEQUENCE CHARACTERISTICS:

(A) LENGTH: 6 base pairs
            (B) TYPE: nucleic acid
            (C) STRANDEDNESS: single
            (D) TOPOLOGY: linear (xi) SEQUENCE DESCRIPTION: SEQ ID NO:4:

TGGCCA                                                                    6

(2) INFORMATION FOR SEQ ID NO:5:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (xi) SEQUENCE DESCRIPTION: SEQ ID NO:5:

GCAAGCNNNN NNNN                                                          14

(2) INFORMATION FOR SEQ ID NO:6:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:6:

CGTCGNNNNN NNNNNNN                                                       17

(2) INFORMATION FOR SEQ ID NO:7:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (xi) SEQUENCE DESCRIPTION: SEQ ID NO:7:

GCCNNNNNGG C                                                             11

(2) INFORMATION FOR SEQ ID NO:8:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (xi) SEQUENCE DESCRIPTION: SEQ ID NO:8:

CCANNNNNNT GG                                                            12

(2) INFORMATION FOR SEQ ID NO:9:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (xi) SEQUENCE DESCRIPTION: SEQ ID NO:9:

CCANNNNNNT GG                                                            12

(2) INFORMATION FOR SEQ ID NO:10:

(i) SEQUENCE CHARACTERISTICS:
            (A) LENGTH: 6 base pairs (B) TYPE: nucleic acid
            (C) STRANDEDNESS: single
            (D) TOPOLOGY: linear (xi) SEQUENCE DESCRIPTION: SEQ ID NO:10:

AGCGCT                                                                          6

(2) INFORMATION FOR SEQ ID NO:11:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (xi) SEQUENCE DESCRIPTION: SEQ ID NO:11:

GAGNNNNNNN GTCA                                                                 14

(2) INFORMATION FOR SEQ ID NO:12:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:12:

TGANNNNNNN NTGCT                                                                15

(2) INFORMATION FOR SEQ ID NO:13:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:13:

ATCANNNNNN NATTC                                                                15

(2) INFORMATION FOR SEQ ID NO:14:

(i) SEQUENCE CHARACTERISTICS:
            (A) LENGTH: 6 base pairs
            (B) TYPE: nucleic acid
            (C) STRANDEDNESS: single
            (D) TOPOLOGY: linear (xi) SEQUENCE DESCRIPTION: SEQ ID NO:14:

TACGTA                                                                          6

(2) INFORMATION FOR SEQ ID NO:15:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (xi) SEQUENCE DESCRIPTION: SEQ ID NO:15:

CCTNNNNNAG G                                                                    11

(2) INFORMATION FOR SEQ ID NO:16:

(i) SEQUENCE CHARACTERISTICS:
            (A) LENGTH: 6 base pairs
            (B) TYPE: nucleic acid

```
            (C) STRANDEDNESS: single
            (D) TOPOLOGY: linear (xi) SEQUENCE DESCRIPTION: SEQ ID NO:16:

GATAGC                                                                          6

(2) INFORMATION FOR SEQ ID NO:17:

(i) SEQUENCE CHARACTERISTICS:
            (A) LENGTH: 6 base pairs
            (B) TYPE: nucleic acid
            (C) STRANDEDNESS: single
            (D) TOPOLOGY: linear (xi) SEQUENCE DESCRIPTION: SEQ ID NO:17:

GATAGC                                                                          6

(2) INFORMATION FOR SEQ ID NO:18:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (xi) SEQUENCE DESCRIPTION: SEQ ID NO:18:

GGATGNNNNN NNNN                                                                14

(2) INFORMATION FOR SEQ ID NO:19:

(i) SEQUENCE CHARACTERISTICS:
            (A) LENGTH: 6 base pairs
            (B) TYPE: nucleic acid
            (C) STRANDEDNESS: single
            (D) TOPOLOGY: linear (xi) SEQUENCE DESCRIPTION: SEQ ID NO:19:

WGGCCW                                                                          6

(2) INFORMATION FOR SEQ ID NO:20:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:20:

GACGCNNNNN NNNNN                                                               15

(2) INFORMATION FOR SEQ ID NO:21:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:21:

GACGCNNNNN NNNNN                                                               15

(2) INFORMATION FOR SEQ ID NO:22:

(i) SEQUENCE CHARACTERISTICS:
            (A) LENGTH: 6 base pairs
            (B) TYPE: nucleic acid
            (C) STRANDEDNESS: single
```

(D) TOPOLOGY: linear (xi) SEQUENCE DESCRIPTION: SEQ ID NO:22:

GTTAAC                                                                    6

(2) INFORMATION FOR SEQ ID NO:23:

(i) SEQUENCE CHARACTERISTICS:
          (A) LENGTH: 6 base pairs
          (B) TYPE: nucleic acid
          (C) STRANDEDNESS: single
          (D) TOPOLOGY: linear (xi) SEQUENCE DESCRIPTION: SEQ ID NO:23:

TGCGCA                                                                    6

(2) INFORMATION FOR SEQ ID NO:24:

(i) SEQUENCE CHARACTERISTICS:
          (A) LENGTH: 6 base pairs
          (B) TYPE: nucleic acid
          (C) STRANDEDNESS: single
          (D) TOPOLOGY: linear (xi) SEQUENCE DESCRIPTION: SEQ ID NO:24:

GCCGGC                                                                    6

(2) INFORMATION FOR SEQ ID NO:25:

(i) SEQUENCE CHARACTERISTICS:
          (A) LENGTH: 6 base pairs
          (B) TYPE: nucleic acid
          (C) STRANDEDNESS: single
          (D) TOPOLOGY: linear (xi) SEQUENCE DESCRIPTION: SEQ ID NO:25:

GGCGCC                                                                    6

(2) INFORMATION FOR SEQ ID NO:26:

(i) SEQUENCE CHARACTERISTICS:
          (A) LENGTH: 6 base pairs
          (B) TYPE: nucleic acid
          (C) STRANDEDNESS: single
          (D) TOPOLOGY: linear (xi) SEQUENCE DESCRIPTION: SEQ ID NO:26:

TCGCGA                                                                    6

(2) INFORMATION FOR SEQ ID NO:27:

(i) SEQUENCE CHARACTERISTICS:
          (A) LENGTH: 6 base pairs
          (B) TYPE: nucleic acid
          (C) STRANDEDNESS: single
          (D) TOPOLOGY: linear (xi) SEQUENCE DESCRIPTION: SEQ ID NO:27:

CMGCKG                                                                    6

(2) INFORMATION FOR SEQ ID NO:28:

(i) SEQUENCE CHARACTERISTICS:
          (A) LENGTH: 6 base pairs
          (B) TYPE: nucleic acid
          (C) STRANDEDNESS: single
          (D) TOPOLOGY: linear (xi) SEQUENCE DESCRIPTION: SEQ ID NO:28:

CAGCTG                                                                          6

(2) INFORMATION FOR SEQ ID NO:29:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (xi) SEQUENCE DESCRIPTION: SEQ ID NO:29:

CAGCTG                                                                          6

(2) INFORMATION FOR SEQ ID NO:30:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (xi) SEQUENCE DESCRIPTION: SEQ ID NO:30:

AGTACT                                                                          6

(2) INFORMATION FOR SEQ ID NO:31:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:31:

GGCCNNNNNG GCC                                                                 13

(2) INFORMATION FOR SEQ ID NO:32:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (xi) SEQUENCE DESCRIPTION: SEQ ID NO:32:

CCCGGG                                                                          6

(2) INFORMATION FOR SEQ ID NO:33:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (xi) SEQUENCE DESCRIPTION: SEQ ID NO:33:

TACGTA                                                                          6

(2) INFORMATION FOR SEQ ID NO:34:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (xi) SEQUENCE DESCRIPTION: SEQ ID NO:34:

AGGCCT                                                                                6

(2) INFORMATION FOR SEQ ID NO:35:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (xi) SEQUENCE DESCRIPTION: SEQ ID NO:35:

GACNNNGTC                                                                             9

(2) INFORMATION FOR SEQ ID NO:36:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:36:

GAANNNNTTC                                                                           10

(2) INFORMATION FOR SEQ ID NO:37:

(i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO:37:

Pro Ala Gly Pro
 1

(2) INFORMATION FOR SEQ ID NO:38:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:38:

Pro Phe His Leu Leu Val Tyr Ser
 1               5

(2) INFORMATION FOR SEQ ID NO:39:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:39:

Val Asp Asp Asp Asp Lys
 1               5

(2) INFORMATION FOR SEQ ID NO:40:

(i) SEQUENCE CHARACTERISTICS:
            (A) LENGTH: 13 amino acids
            (B) TYPE: amino acid
            (C) STRANDEDNESS: single

```
        (D) TOPOLOGY: linear (xi) SEQUENCE DESCRIPTION: SEQ ID NO:40:

Met Arg Ile Gln Ala Phe Pro Val Asp Asp Asp Lys
1               5                   10
```

Modifications of the above-described modes for carrying out the invention that are obvious to persons of skill in this field are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for performing target amplification in an assay system comprising an assay medium, said assay system being useful for determining the presence of a target nucleic acid having a target nucleic acid sequence in a sample suspected of containing said target nucleic acid, comprising the steps of:
   a) providing in said assay system a target analog nucleic acid-anchor complex, wherein said target analog nucleic acid has a target analog nucleic acid sequence that is essentially the same as the target nucleic acid sequence, and wherein said anchor prevents said target analog nucleic acid from becoming released into said assay medium in the absence of said target nucleic acid;
   b) adding said sample to said assay system under conditions which allow said target analog nucleic acid-anchor complex to be cleaved in the presence of target nucleic acid in said sample thereby releasing said target analog nucleic acid into said assay medium;
   c) providing in said assay system a signal generator which generates detectable signal from the presence of said target nucleic acid and said released target analog nucleic acid, thereby amplifying the amount of target nucleic acid present in said assay system; and
   d) detecting the presence of detectable signal to thereby determine the presence of said target nucleic acid.

2. The method according to claim 1, wherein said target nucleic acid comprises DNA.

3. The method according to claim 1, wherein said target nucleic acid comprises RNA.

4. The method according to claim 1, wherein said target nucleic acid comprises double-stranded DNA.

5. The method according to claim 1, wherein said anchor is a protein.

6. The method according to claim 5, wherein said protein is a zymogen.

7. The method according to claim 6, wherein said zymogen is trypsinogen.

8. The method according to claim 1, wherein said anchor is a polysaccharide.

9. The method of claim 6, further comprising the step of stabilizing the zymogen.

10. The method according to claim 9, wherein said stabilization is effected by covalent modification of the zymogen with polyethylene glycol.

11. The method according to claim 9, wherein said zymogen has been mutated such that a lysine residue has been replaced by an arginine, thereby preserving a protease cleavage site.

12. The method according to claim 9, wherein said stabilization is effected by covalent modification of the zymogen with guanidine.

13. The method according to claim 6, wherein said zymogen has a cysteine residue at a position amino-terminal to an activator cleavage site, said cysteine residue serving as an attachment site for a linker arm which binds said target analog nucleic acid.

14. The method according to claim 6, wherein said zymogen has been mutated to contain said cysteine residue.

15. The method of claim 1, wherein said anchor is a nucleic acid.

16. The method of claim 15, wherein said anchor is a double-stranded DNA.

17. A method for increasing the sensitivity of an assay for detecting a target nucleic acid in a sample by releasing a target nucleic acid analog into an assay medium in the presence of the target nucleic acid, wherein the target nucleic analog generates a signal similarly with that of the target nucleic acid, thereby amplifying the amount of nucleic acid which is detected in the assay, comprising the steps of:
   a) providing an assay system comprising:
      i) a signal generator, wherein said signal generator generates a detectable signal in the presence of said target nucleic acid and released target nucleic acid analog;
      ii) a bound target nucleic acid analog that is unable to generate detectable signal from said signal generator unless the target nucleic acid analog is released; and
   b) adding said sample to said assay system under conditions wherein the presence of said target nucleic acid from said sample releases said target nucleic acid analog which results in generation of a detectable signal, thereby increasing detectability of the target nucleic acid by amplifying the amount of nucleic acid that generates signal from the signal generator.

18. The method of claim 17, wherein the target nucleic acid and the target nucleic acid comprise an essentially similar nucleotide sequence such that a single nucleic acid probe can hybridize to both the target nucleic acid and the target analog nucleic acid.

19. The method according to claim 17, wherein said target nucleic acid comprises DNA.

20. The method according to claim 17, wherein said target nucleic acid comprises RNA.

21. The method according to claim 17, wherein said target nucleic acid comprises double-stranded DNA.

22. The method according to claim 17, wherein said bound nucleic acid target analog is bound to a protein.

23. The method according to claim 22, wherein said protein is a zymogen.

24. The method according to claim 23, wherein said zymogen is trypsinogen.

25. The method according to claim 17, wherein said bound nucleic acid target analog is bound to a polysaccharide or a protein.

26. The method according to claim 23, further comprising the step of stabilizing the zymogen.

27. The method according to claim 26, wherein said stabilization is effected by covalent modification of the zymogen with polyethylene glycol.

28. The method according to claim 26, wherein said zymogen has been mutated such that a lysine residue has been replaced by an arginine, thereby preserving a protease cleavage site.

29. The method according to claim 26, wherein said stabilization is effected by covalent modification of the zymogen with guanidine.

30. The method according to claim 23, wherein said zymogen has a cysteine residue at a position amino-terminal to an activator cleavage site, said cysteine residue serving as an attachment site for a linker arm which links said protein to said nucleic acid target analog.

31. The method according to claim 24, wherein said zymogen has been mutated to contain said cysteine residue.

32. The method of claim 19, wherein said bound nucleic acid target analog is bound to a nucleic acid.

33. The method of claim 32, wherein said anchor is a double-stranded DNA.

34. The method of claim 17 for increasing the sensitivity of an assay by amplifying the amount of nucleic acid which is detected in the assay through target cycling, further comprising a bound activator molecule that is released upon contact with either said target nucleic acid or said target nucleic acid analog, wherein the released activator molecule causes release of said target nucleic acid analog, whereby the amount of nucleic acid which is detected is amplified by cycling target nucleic acid.

* * * * *